(12) United States Patent
Soltani et al.

(10) Patent No.: US 11,537,205 B2
(45) Date of Patent: Dec. 27, 2022

(54) WIRELESS POWER AND DATA TRANSMISSION SYSTEM FOR WEARABLE AND IMPLANTABLE DEVICES

(71) Applicant: THE GOVERNING COUNCIL OF THE UNIVERSITY OF TORONTO, Toronto (CA)

(72) Inventors: Nima Soltani, Toronto (CA); Roman Genov, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 17/322,162

(22) Filed: May 17, 2021

(65) Prior Publication Data

US 2021/0278901 A1    Sep. 9, 2021

Related U.S. Application Data

(62) Division of application No. 15/766,402, filed as application No. PCT/CA2016/051169 on Oct. 7, 2016, now Pat. No. 11,036,294.

(Continued)

(51) Int. Cl.
*G06F 3/01* (2006.01)
*H02J 50/12* (2016.01)
(Continued)

(52) U.S. Cl.
CPC .......... *G06F 3/015* (2013.01); *A61N 1/36132* (2013.01); *A61N 1/3787* (2013.01);
(Continued)

(58) Field of Classification Search
CPC ........... G06F 3/015; H02J 50/12; H02J 7/025; A61N 1/37223; A61N 1/3787;
(Continued)

(56) References Cited

U.S. PATENT DOCUMENTS

| 6,597,954 B1 | 7/2003 | Pless et al. |
| 7,212,110 B1 | 5/2007 | Martin et al. |
| (Continued) | | |

FOREIGN PATENT DOCUMENTS

| CN | 102157989 A | 8/2011 |
| WO | 2008/109508 A2 | 9/2008 |
| WO | 2015092747 A2 | 6/2015 |

OTHER PUBLICATIONS

"Design of an Optimal & Closed-Loop Neurostimulation System for treatment of Epilepsy" Gao, Richard, [online], Nov. 23, 2015 (Nov. 23, 2015]., Retrieved on Oct. 12, 2017 (Oct. 12, 2017). Retrieved from: http:www,undergraduatelibrary.org/2014/medical-sciences/design-optimal-closed-loop-neuromodulation-system-treatment-epilepsy.

(Continued)

*Primary Examiner* — Carlos Amaya
(74) *Attorney, Agent, or Firm* — Bhole IP Law; Anil Bhole; Marc Lampert

(57) ABSTRACT

In one aspect, an electronic device for continuous and simultaneous powering and data transfer is provided, the electronic device comprising: an inductive power receiver operable to generate a power signal from a sensed magnetic field, the power signal; an LC tank and diode pair electrically coupled to the power receiver and operable to obtain the power signal, the LC tank and diode pair cooperating to generate a corresponding clipped signal thereof; and an antenna comprising a high-pass filter, the antenna electrically coupled to the diode pair and operable to emit a pulse-train by high-pass filtering the clipped signal.

8 Claims, 18 Drawing Sheets

Related U.S. Application Data

(60) Provisional application No. 62/238,271, filed on Oct. 7, 2015.

(51) Int. Cl.
| | | |
|---|---|---|
| *A61N 1/36* | (2006.01) | |
| *A61N 1/372* | (2006.01) | |
| *A61N 1/378* | (2006.01) | |
| *G01S 13/02* | (2006.01) | |
| *H04B 5/00* | (2006.01) | |
| *H02J 7/02* | (2016.01) | |

(52) U.S. Cl.
CPC ...... *A61N 1/37223* (2013.01); *G01S 13/0209* (2013.01); *H02J 7/025* (2013.01); *H02J 50/12* (2016.02); *H04B 5/0031* (2013.01); *H04B 5/0037* (2013.01); *H04B 5/0043* (2013.01)

(58) Field of Classification Search
CPC ............. G01S 13/0209; H04B 5/0031; H04B 5/0037; H04B 5/0043
See application file for complete search history.

(56) References Cited

U.S. PATENT DOCUMENTS

| | | | |
|---|---|---|---|
| 8,180,452 | B2 | 5/2012 | Shaquer |
| 9,030,239 | B1 | 5/2015 | Dastgheib et al. |
| 2002/0172069 | A1 | 11/2002 | Thompson et al. |
| 2004/0068199 | A1 | 4/2004 | Echauz et al. |
| 2005/0075282 | A1 | 4/2005 | Coulter |
| 2005/0197590 | A1 | 9/2005 | Osorio et al. |
| 2007/0050046 | A1 | 3/2007 | Georgopoulos |
| 2007/0067003 | A1 | 3/2007 | Sanchez et al. |
| 2007/0150024 | A1 | 6/2007 | Leyde et al. |
| 2007/0213786 | A1 | 9/2007 | Sackellares et al. |
| 2008/0039904 | A1 | 2/2008 | Bulkes et al. |
| 2008/0176271 | A1 | 7/2008 | Silver et al. |
| 2009/0079607 | A1 | 3/2009 | Denison et al. |
| 2010/0168603 | A1 | 7/2010 | Himes et al. |
| 2010/0197524 | A1 | 8/2010 | Janata et al. |
| 2010/0274321 | A1 | 10/2010 | Libbus |
| 2011/0004268 | A1 | 1/2011 | Tcheng et al. |
| 2011/0130797 | A1 | 6/2011 | Talathi et al. |
| 2011/0306847 | A1 | 12/2011 | Lowry et al. |
| 2012/0053449 | A1 | 3/2012 | Moses et al. |
| 2012/0078071 | A1 | 3/2012 | Bohm et al. |
| 2012/0283800 | A1 | 11/2012 | Perryman et al. |
| 2013/0035745 | A1 | 2/2013 | Ahmed |
| 2013/0172774 | A1 | 7/2013 | Crowder et al. |
| 2013/0178731 | A1 | 7/2013 | Bosl |
| 2014/0012122 | A1 | 1/2014 | Sadek et al. |
| 2014/0081094 | A1 | 3/2014 | Jordan et al. |
| 2014/0213874 | A1 | 7/2014 | Tong et al. |
| 2014/0257128 | A1 | 9/2014 | Moxon et al. |
| 2014/0267163 | A1 | 9/2014 | Hotelling |
| 2014/0336948 | A1 | 11/2014 | Qin et al. |
| 2014/0371515 | A1 | 12/2014 | John |
| 2014/0379046 | A1 | 12/2014 | Tcheng et al. |
| 2014/0379620 | A1 | 12/2014 | Sarrafzadeh et al. |
| 2015/0012111 | A1 | 1/2015 | Contreras-Vidal et al. |
| 2015/0206051 | A1 | 7/2015 | McIntosh et al. |
| 2016/0089540 | A1 | 3/2016 | Bolea |
| 2018/0269896 | A1 | 9/2018 | Ouzounov et al. |
| 2019/0059803 | A1 | 2/2019 | Myers et al. |
| 2019/0076587 | A1* | 3/2019 | Rudser ............... A61M 60/871 |
| 2019/0143119 | A1 | 5/2019 | Dzirasa |
| 2019/0150774 | A1 | 5/2019 | Brinkmann et al. |
| 2019/0314564 | A1 | 10/2019 | Rudser et al. |
| 2020/0195055 | A1* | 6/2020 | Hansen ................... H02J 50/40 |

OTHER PUBLICATIONS

"Micropower CMOS Integrated Low-Noise Amplification, Filtering, and Digitization of Multimodal Neuropotentials" Mollazadeh et al. [online], Jan. 1, 2010 (Jan. 1, 2010)., Retrieved Oct. 12, 2017 (Oct. 12, 2017). Retrieved from: https://www.ncbi.nlm.nih.gov/pmc/articles/PMC2747318/.

"The 128-Channel Fully Differential Digital Integrated Neural Recording and Stimulation Interface" Shahrokhi et al [online], May 24, 2010 (May 24, 2010), [Retrieved on Oct. 12, 2017 (Oct. 12, 2017)., Retrieved from: http://ieeexplore.ieee.org/document/5471738/authors?part=1.

"Advisory Action for U.S. Appl. No. 15/177,615; USPTO; dated Oct. 12, 2018."

"Advisory Action for U.S. Appl. No. 15/177,615; USPTO; dated Jan. 30, 2019."

"Bagheri, A., et al. (2013) Massively-Parallel Neuromonitoring and Neurostimulation Rodent Headset With Nanotextured Flexible Microelectrodes. IEEE Transactions on Biomedical Circuits and Systems, 7:601-609".

"Colpan, M.E., et al., (2007) Proportional Feedback Stimulation for Seizure Control in Rats. Epilepsia, 48:1594-1603."

"European Search Opinion for 16852943.6, dated Apr. 24, 2019."

"European Search Opinion for EU patent application No. 16806476.4, EPO, dated Jun. 18, 2019."

"European Search Opinion for EU patent application No. 17830150.3, EPO, dated May 8, 2020."

"Extended European Search Report for 16852943.6, European Patent Office, dated Apr. 24, 2019."

"Good, L.B. et al., (2009) Control of Synchronization of Brain Dynamics Leads to Control of Epileptic Seizures in Rodents. International Journal of Neural Systems, 19:173-196."

"International Search Report corresponding to PCT/CA2016/050655; Canadian Intellectual Property Office; dated Sep. 7, 2016."

"International Search Report corresponding to PCT/CA2017/050867; Canadian Intellectual Property Office; dated Oct. 18, 2017."

"International Search Report for PCT/CA2016/051169, Canadian Intellectual Property Office, dated Jan. 13, 2017."

"Jiruska, P., et al. (2010) Effects of Direct Brain Stimulation Depend on Seizure Dynamics. Epilepsia 51:93-97."

"Koubeissi, M.Z. et al., (2013) Low-Frequency Electrical Stimulation of a Tiber Tract in Temporal Lobe Epilepsy. Annals of Neurology, 74:223-231."

"Krook-Magnuson, E., et al. (2013) On-Demand Optogenetic Control of Spontaneous Seizures in Temporal Lobe Epilepsy. Nature Communications, 4:1376."

"Lockman, J., Fisher, R.S. (2009) Therapeutic Brain Stimulation for Epilepsy. Neurologic Clinics 27:1031-1040."

"Medeiros, D.D., Moraes M.F. (2014) Focus on Desynchronization Rather Than Excitability: A New Strategy for Intraencephalic Electrical Stimulation. Epilepsy Behav, 38C:32-36."

"Office action for U.S. Appl. No. 15/580,823, United States Patent & Trademark Office, dated Sep. 3, 2020."

"Office Action for U.S. Appl. No. 15/766,402, United States Patent & Trademark Office, dated Jul. 31, 2020."

"Office Action for U.S. Appl. No. 16/312,467, United States Patent & Trademark Office, dated Jul. 23, 2020."

"Office Action for U.S. Appl. No. 15/177,615; USPTO; dated Oct. 6, 2017."

"Office Action for U.S. Appl. No. 15/177,615; USPTO; dated Aug. 9, 2018."

"Office Action for U.S. Appl. No. 15/177,615; USPTO; dated Nov. 1, 2018".

"Office Action for U.S. Appl. No. 15/177,615; USPTO; dated Dec. 31, 2018."

"Osorio, I., Frei M.G. (2009) Seizure Abatement With Single DC Pulses: Is Phase Resetting at Play? International Journal of Neural Systems, 19:149-156."

"Panagiotis Kassanos et al: ACMOS Magnitude/Phase Measurement Chip for Impedance Spectroscopy, IEEE Sensors Journal, vol. 13, No. 6, Jun. 2013."

"Rashid, S. et al. (2012)Low Frequency Stimulation of Ventral Hippocampal Commissures Reduces Seizures in a Rat Model of Chronic Temporal Lobe Epilepsy. Epilepsia, 53:147-156."

(56) References Cited

OTHER PUBLICATIONS

"Schindler et al., "Increasing synchronization may promote seizure termination: Evidence from status epilepticus", Jun. 18, 2007, Clinical Neurophysiology, 118, 1955-1968."
"Sun, F.T., Morrell, M.J. (2014) The RNS System: Responsive Cortical Stimulation for the Treatment of Refractory Partial Epilepsy. Expert Review of Medical Devices, 11:563-572."
"Supplementary European Search Report for EU patent application No. 16806476.4, EPO, dated Jun. 18, 2019."
"Supplementary European Search Report for EU patent application No. 17830150.3, EPO, dated May 8, 2020."
"Supplementary Partial European Search Report for EU patent application No. 16806476.4, EPO, dated Feb. 14, 2019."
"Tergau, F., et al. (1999) Low-Frequency Repetitive Transcranial Magnetic Stimulation Improves Intractable Epilepsy. Lancet, 353:2209."
"Weiss, S.R., et al., (1995) Quenching: Inhibition of Development and Expression of Amygdala Kindled Seizures With Low Frequency Stimulation. Neuroreport, 6:2171-2176."
"Written Opinion for PCT/CA2016/051169, Canadian Intellectual Property Office, dated Jan. 13, 2017."
"Written Opinion of the International Searching Authority corresponding to PCT/CA2016/050655; Canadian Intellectual Property Office; dated Sep. 7, 2016."
"Written Opinion of the International Searching Authority corresponding to PCT/CA2017/050867; Canadian Intellectual Property Office; dated Oct. 18, 2018."
Abdelhalim, Karim, et al., "64-Channel UWB Wireless Neural Vector Analyzer SOC With a Neurostimulator", IEEE Journal of Solid-state circuits, IEEE, USA, vol. 48, No. 10, Oct. 1, 2013, 2494-2510.
Kassiri Hossein, et al., "Inductively-powered direct coupled 64-channel chopper-stabilized epilepsy-responsive neurostimulator with digital offset cancellation and tri-band radio."
Soltani Nima, et al., "Cellular inductive powering system for weakly-linked resonant rodent implant", 2013 IEE Biomedical Circuits and Systems Conference (BIOCAS), IEEE, Oct. 31, 2013 (Oct. 31, 2013), pp. 350-353.
Office Action for U.S. Pat. No. 2,988,789, CIPO, dated Jun. 22, 2022.

* cited by examiner

WIRELESS POWER AND DATA TRANSMISSION SYSTEM FOR WEARABLE AND IMPLANTABLE DEVICES

TECHNICAL FIELD

The following relates generally to wireless power and data systems and more specifically to a wireless power and data transmission system suitable for wearable and implantable devices.

BACKGROUND

Wearable electronic devices are becoming ubiquitous. Additionally, the use of "electroceuticals"—that is, implantable electronics, commonly in the medical sensor industry—is also increasing. Such devices are typically worn on or implanted within a human or animal body.

Such devices may be wired or wireless. In wired cases, the devices are only operable when wired to a power source, which presents a clear limitation on mobility of the human or animal wearing or implanted with the device. In wireless cases, the devices may not incorporate battery power. If battery power is the primary source of power, typically wireless data transmission would usually be minimized, to extend the life of the battery and require little or no charging over the useable lifetime of the device, as charging would require a period of wiring or removal of the device from the wearer, which might be difficult or impossible. If battery power is not the primary source of power, then a wireless powering mechanism is always needed to activate the device, in which case the device typically needs to remain in close proximity to a power transmitter.

There is a desire to enable wireless powering (and consequently charging of any reserve battery, if one is provided) for such devices, particularly implantables, which can be difficult to remove for charging, and can be difficult to regulate when wirelessly powered. In cases where such devices are designed to provide wireless data transmission, it can be expected that such transmission requires significant power, in which case most existing forms of wireless powering is not suitable and wired powering/charging is also not realistic.

For the foregoing reasons, it is desirable to provide both wireless power and data transmission between a remote transfer device and the wearable or implantable device.

There are existing solutions for providing wireless power and data transmission. A common example is use of RFID and other wireless sensory domains. A typical RFID implementation comprises a powering device/data receiver which wirelessly transmits power to an RFID tag/sensor, wherein upon the RFID (or other) tag/sensor receiving power, it transmits data to the data receiver contemporaneously. However, in most of these implementations, the read range is to a great extent limited by the phase noise performance of oscillators. Other techniques such as active transmission and time-multiplexing (duty-cycling) are more power-consuming than RFID which effectively reduce the average bandwidth of the wireless link. Further, RFID is generally considered to have a relatively low data bandwidth and, therefore, is not particularly suitable to high data volume applications.

Therefore, most such solutions are not suitable for transmission over greater distances; and high-volume wireless data transmission without running down the battery, or possibly requiring frequent wired charging, which is not realistic in many cases. For example, in chronic disease studies, it is typical to affix a wearable or implantable device to a laboratory animal and continuously monitor the laboratory animals wherein the animal is free to move around during its normal day to day activities without being tied to power and/or data cables.

Further, in wireless power transfer applications, most existing techniques aim to maximize the efficiency of power transfer from a transmitter to a receiver. In other words, good wireless power transfer design is considered to be one that delivers the highest power from a fixed power source. However, in human and animal applications (where the human or animal is present near the device like in biomedical and body area networks), the maximum power is effectively limited by the human and animal safety limits rather than source power availability. Safety is a major concern in the inductive power transfer technology. For biomedical and consumer market applications, observing the specific absorption rate (SAR) limit set by regulations and guidelines is a critical design objective.

SUMMARY

In one aspect, an apparatus for wireless power and data communication incorporating an implantable or wearable electronic device is provided, the apparatus comprising: a powering medium comprising a transmission coil electrically coupled to a source providing a power signal and a data signal, the powering medium generating a magnetic field for transmitting the power signal and the data signal wirelessly by the transmission coil; an implantable or wearable inductively powered device comprising a wireless interface communicatively coupled to an application circuit, the wireless interface comprising an inductive receiving circuit including an inductive data receiver and inductive power receiver, and a pulse radio transmitter, the inductive power receiver configured to receive the wirelessly transmitted power signal and data signal and provide the received power signal and data signal to the application circuit, and to transmit data received from the application circuit by an antenna; a receiver in communication with a computer for receiving the data and providing the data to a processor; and a computer comprising the source and the processor.

In another aspect, a method for wirelessly powering and communicating with an implantable or wearable electronic device is provided, the method comprising: wirelessly transmitting a power signal and a data signal via a magnetic field generated by a transmission coil electrically coupled to a source providing the power signal and the data signal; receiving the wirelessly transmitted power signal and data signal at the implantable or wearable inductively powered device using an inductive data receiver and an inductive power receiver; communicating the power signal and the data signal from the an inductive data receiver and inductive power receiver to an application circuit, the application circuit configured to generate data; transmitting the data by an antenna; and receiving the transmitted data at a receiver and providing the data to a computer comprising a processor.

In another aspect, an electronic device for continuous and simultaneous powering and data transfer is provided, the electronic device comprising: an inductive power receiver comprising a resonator having a coil for receiving an externally induced magnetic field and correspondingly generating a resonating current; a rectifier electrically coupled to the inductive power receiver to convert and store a portion of the resonating current to a DC voltage; a limiter electrically coupled to the rectifier for limiting the DC voltage to a threshold voltage to produce a clipped signal thereof; and an antenna electrically coupled to the limiter and configured to emit a pulse-train corresponding to the clipped signal.

In another aspect, a method for optimizing the geometries of magnetic coils is provided, the method comprising maximizing a coil fill factor and a number of turns until a fraction power lost in a biological medium is minimized.

In another aspect, a method for arranging receiving coils is provided, the method comprising stacking a plurality of flexible printed circuit coils to divide energy loss corresponding to a number of stacked coils.

In another aspect, a data transmission circuit is provided, the circuit comprising: an input for receiving a pulse train at a first frequency; an oscillator comprising a switch toggling a digitally-controlled cross-coupled LC tank and a diode pair to produce a clipped pulse train; and a data transmitter configured to receive, from an application circuit, a baseband data stream for transmission, a delay lock loop and to align the baseband data stream to the pulse train, and a stream generator to generate a transmission stream by operating on the data stream with the pulse train.

In another aspect, an electronic device for continuous and simultaneous powering and data transfer is provided, the electronic device comprising: an inductive power receiver operable to generate a power signal from a sensed magnetic field, the power signal; an LC tank and diode pair electrically coupled to the power receiver and operable to obtain the power signal, the LC tank and diode pair cooperating to generate a corresponding clipped signal thereof; and an antenna comprising a high-pass filter, the antenna electrically coupled to the diode pair and operable to emit a pulse-train by high-pass filtering the clipped signal.

In another aspect, an electronic device for continuous and simultaneous powering and high-resolution data transfer from wireless sensor nodes including wireless medical implantable devices is provided.

In another aspect, a radio transmitter which products electrical impulses with minimum power dissipation in the form of heat is provided. The reduction in energy dissipation allows the radio to transmit significantly more data in a unit of time as compared to currently available UWB radio design.

In another aspect, a method of high datarate transmission is provided, the method based on limiting the output swing of a high-Q resonating LC tank and feeding the resulting high-bandwidth signal into a UWB antenna.

In another aspect, a low radiation high-power wireless energy transfer system is provided, the system operable through biological media by minimizing the fraction of energy lost in the medium to received power.

In another aspect, a method for optimizing the geometries of magnetic coils is provided, the method comprising maximizing a coil fill factor and a number of turns until the fraction power lost in a biological medium is minimized.

In another aspect, a method for arranging receiving coils is provided, the method comprising stacking multiple flexible printed circuit coils to divide energy loss corresponding to the number of stacked coils.

In another aspect, a method for manufacturing an integrated magnetic coil on a CMOS substrate for remotely energizing an implantable microchip with alternating magnetic field is provided.

These and other aspects are contemplated and described herein. It will be appreciated that the foregoing summary sets out representative aspects of systems, methods and apparatus for wireless power and data transmission system suitable for wearable and implantable devices to assist skilled readers in understanding the following detailed description

DESCRIPTION OF THE DRAWINGS

A greater understanding of the embodiments will be had with reference to the Figures, in which.

DETAILED DESCRIPTION

Figure 1:
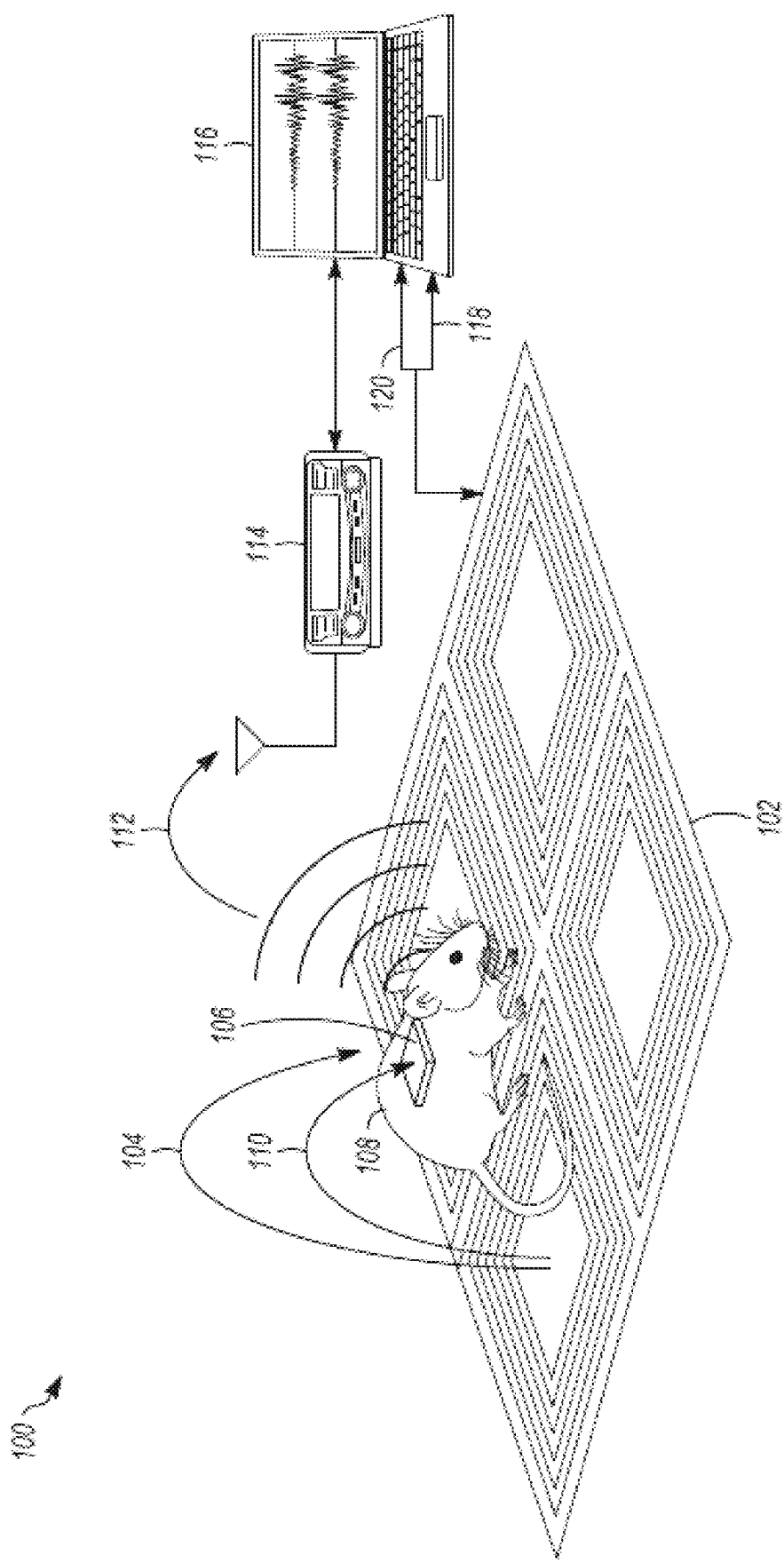
FIG. 1 illustrates an exemplary embodiment of a wireless power and data transmission system for wearable and implantable devices, as applied to a free moving laboratory animal.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

The following provides a wireless power and data transmission system for wearable and implantable devices. The system may comprise transmitter and receiver circuits, and is operable to provide wireless power and data transmission at a greater level within a certain power budget than the aforementioned techniques. Without limitation, the system is particularly suitable for implantable or wearable devices in that one aspect of the design of the system is a counter-intuitive consideration for safety limits applicable to wearable and implantable devices placed on or within humans or animals, even in view of a compromise to power efficiency.

In one aspect, the system comprises a power receiving device providing ultra-wide bandwidth (UWB) data transmission even in view of potential lowering of power efficiency from the power transmitter, but deriving the UWB signal from a lower frequency steady state power signal. This is achieved by use of a diode pair, which further provides isolation between the power circuit and the application (data generating) circuit in a wearable or implantable device.

The system is generally operable with wireless interface sensor and/or actuator systems. There are many applications in laboratory and industrial settings where the mechanical decoupling that an all-wireless interface offers dramatically reduces the impact of the observing instruments on the events being observed. One example of such application is responsive sensory arrays implanted in or worn by a patient, or an animal or human subject participating in a medical experiment.

While the following is described with particular reference to wearable and implantable devices, the system serves as a wireless power and data interface for sensing, imaging, and recording electronics or any other application where analog data is collected from a source external to the circuits (the environment, animal or human body, etc.) and transmitted to an end storage and processing device such as a computer or a network of computers, or to another sensor node to relay the data to an end device.

Referring first to FIG. 1, an example system implementation is shown. The system (100) comprises a powering medium (102) configured as an inductive floor, which provides a magnetic field fora power signal (104) to an implanted inductively powered device (106) on an animal (108). The inductive floor comprises an m×n array of planar inductive coils which transfer power to the device via resonant magnetic induction. In some embodiments, the floor may be configured to actively search through all the coils in the array to find the one closest to the device (106), and powers the device (106) by turning on that coil only. Such a configuration enables long term operability without battery replacement or removal from the power signal, while permitting the animal to be free to move anywhere on the floor without being tied to power and/or data cables.

The device (106) incorporates a wireless interface (shown in FIG. 2) and an application circuit (not shown). The wireless interface is configured to receive the power signal (104), convert the power signal to a DC power supply for the application circuit, provide the power to the application circuit, receive commands (110) from the powering medium and transmit data (112) to a receiver (114). The receiver is in communication with a computer (116) for processing the received data. The computer (116) is further in communication with the powering medium to provide power (118) and commands (120).

The application circuit performs its functions and provides data to the wireless interface for transmission to the receiver (114). An example of an application circuit is a seizure detection, monitoring and avoidance circuit. An exemplary device receives streams of data generated from a plurality neural recording sensors, and transmits it to the laboratory computers. An algorithm analyzes the real-time data from all the neural sensors to determine if a seizure onset is about to happen. In a closed-loop implementation, the computer then alerts the device of the likelihood of a seizure happening soon via the wireless data interface, at which point actuators linked to the wireless device may attempt to stop the seizure using neuro-stimulation.

Figure 2:
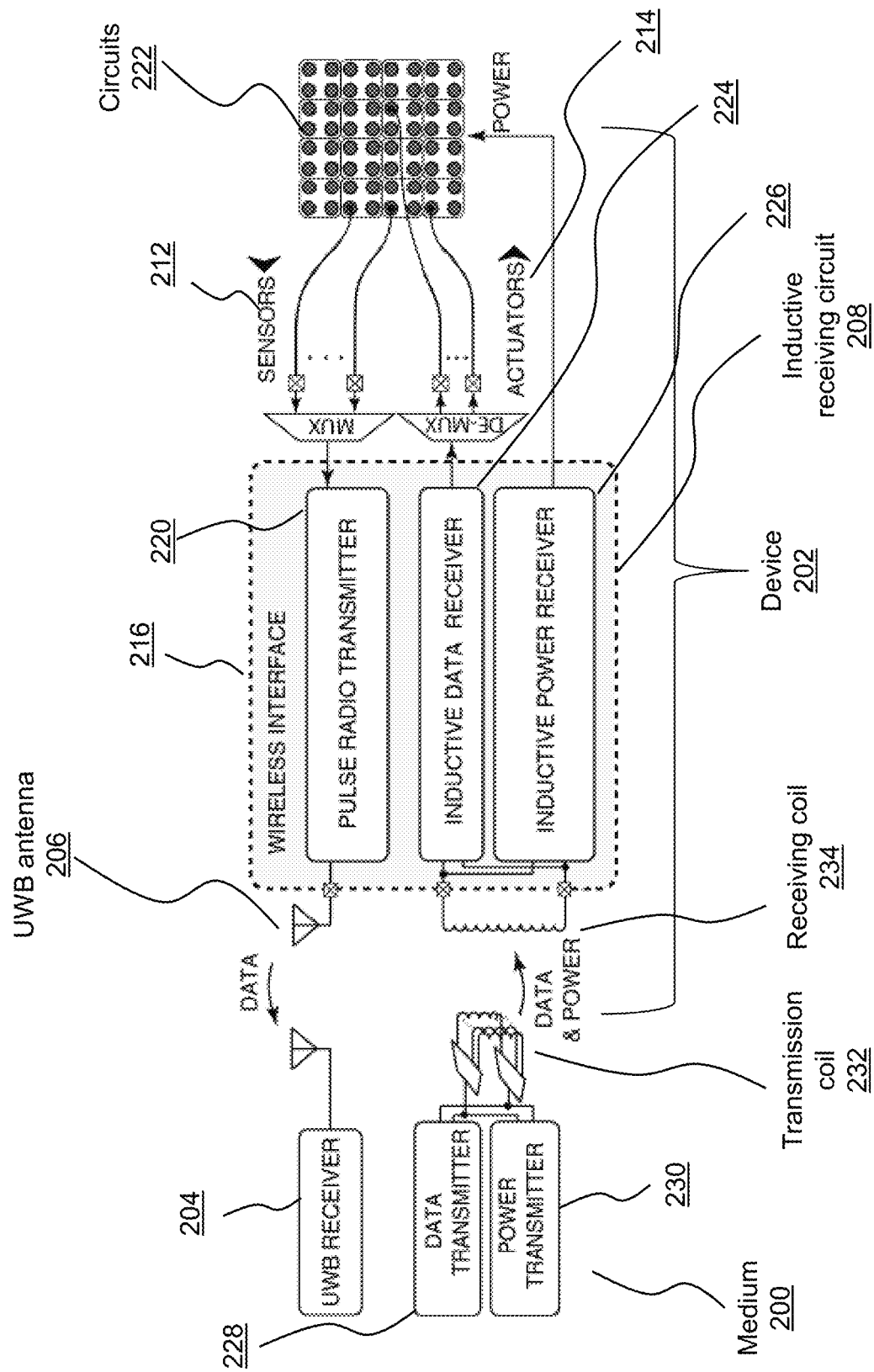
FIG. 2 illustrates an exemplary block diagram of an inductively powered wireless sensor/actuator interface device.

Referring now to FIG. 2, a block diagram of a powering medium (200) and an exemplary inductively powered device (202) is shown. Energy is inductively transferred from the medium (200) to the device (202) by an alternating magnetic field while data is transmitted from the device (202) to the medium (200) or other UWB receiver (204) (which may be located away from the medium) in the form of a pulse train radiated from a UWB antenna (206). A suitable period for the pulse train is in the range of pico or nanosecond.

The medium (200) comprises a data transmitter (228) and power transmitter (230) linked to a transmission coil (232).

As previously noted, the inductively powered device (202) comprises a wireless interface device (216) communicatively coupled to an application circuit (222). The wireless interface device (216) comprises an inductive receiving circuit (208) including an inductive data receiver (224) and inductive power receiver (226), and a pulse radio transmitter (220).

The device (202) is powered by the inductive power receiver (226) which is linked to a receiving coil (234) that harvests energy from an alternating magnetic field created by a power transmitter (230) and radiated by the transmission coil (232). This power is used to operate the sensors (212) and/or actuators (214) interfaced with the wireless interface device (216) as well as all the other circuits (222) within the device (202) itself. The serial data coming from the sensors (212) are sent out to by the pulse radio transmitter (220) to a nearby UWB receiver (204) via UWB antenna (206), which in turn feeds the data to a computer (116) for real-time or offline analysis, and storage.

Figure 3:
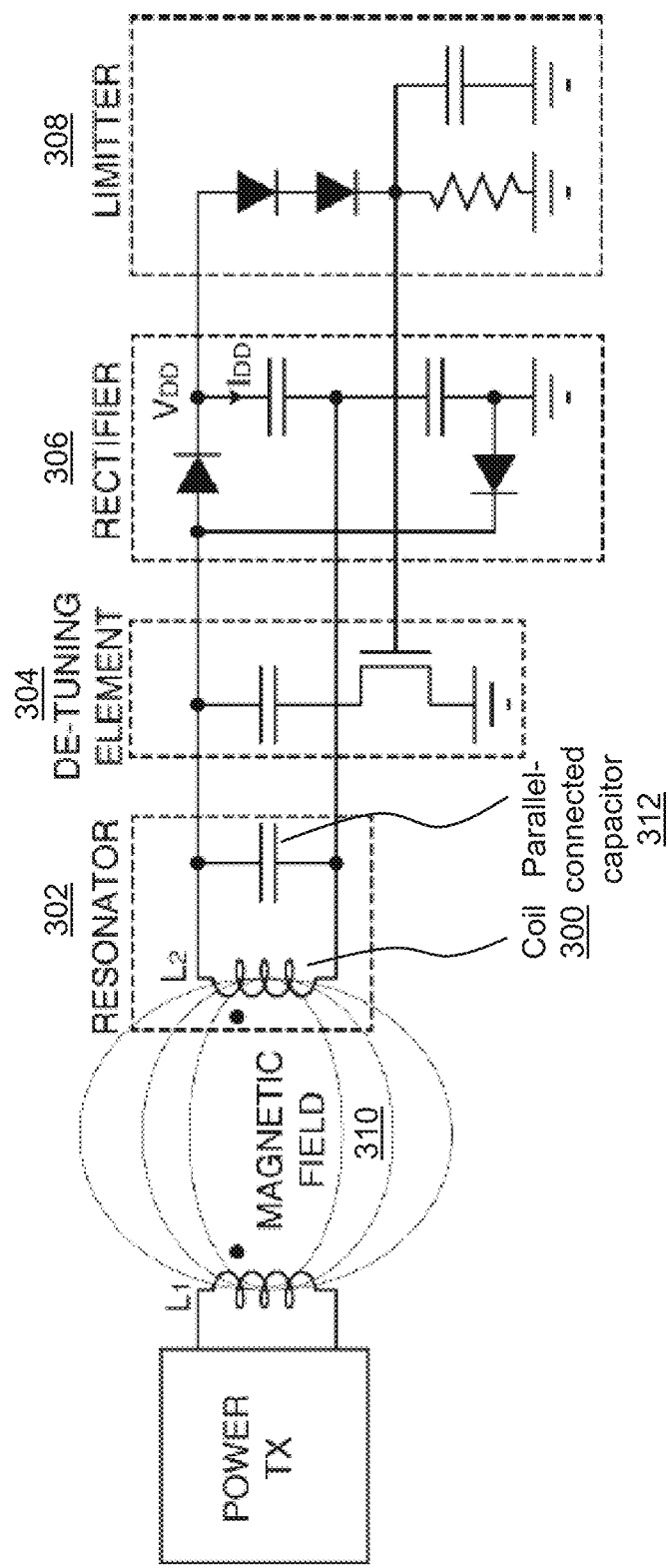
FIG. 3 illustrates an exemplary schematic diagram of an inductive power receiving circuit.

FIG. 3 shows a schematic diagram of an inductive power receiver which converts the energy of the received magnetic field to a usable DC supply. The inductive power receiver shown comprises a resonator (302), de-tuning element (304), rectifier (306) and limiter (308). In the resonator (302), a hollow-core high-inductance magnetic coil (300) is induced with an alternating magnetic field (310), which causes the coil (300) and a parallel-connected capacitor (312) to resonate together at the frequency of the magnetic field (i.e., the coil and the capacitor have the same resonant frequency as the magnetic field). While the coil is resonating, the double-half-wave rectifier (306) converts a portion of the resonating current to a DC voltage and stores it across another capacitor "Cs". The detuning element (304) is optional. The limiter (308) may be provided for overvoltage protection. The limiter discharges the excess charge on the capacitor Cs to prevent the Cs voltage from rising beyond a threshold set by the forward voltages of the 2 series diodes. Without the limiter, the Cs voltage may become too high, which may break down the components in the implant circuits.

The received power signal is used to form a pulse train for transmitting data back from the device. The wireless interface applies UWB backscattering to enable the transmission of a significant amount of data even when the power signal is of a relatively low frequency. Backscattering utilizes the same channel for data transmission as power reception, while applying a different data rate. The present system implements a novel switching circuit to switch the signal window between data transmission and power reception.

Figure 4:
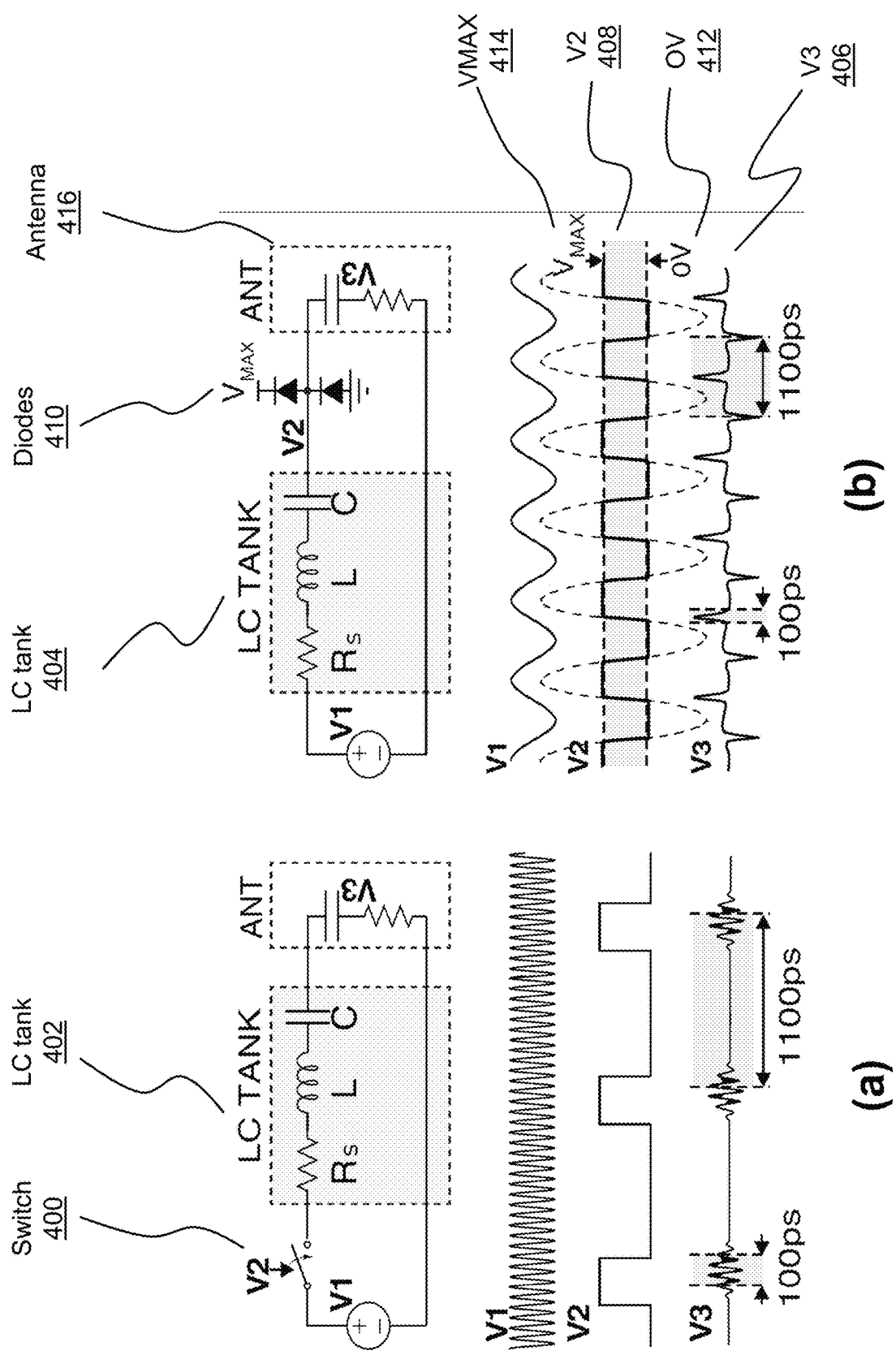
FIG. 4 illustrates two exemplary pulse generation circuits, one using a high-frequency transient and the other a low-frequency steady-state LC tank.

Referring now to FIG. 4, two switching circuits are shown for providing UWB data transmission in a backscattering application. FIG. 4(a) shows a first circuit used in UWB transmitter, and FIG. 4(b) shows a second circuit for a UWB transmitter. With the circuit of FIG. 4(b), in an example where the power signal is provided at around 1.5 MHz, a UWB data transmission rate is possible with the up to two data pulses sent back for each power signal period. Additionally, if the wireless interface incorporates a frequency upconverter, it is possible to achieve data rates at least as high as 250 Mbps.

Ultra-wideband impulse radio (UWB-IR) is in many cases a suitable architecture for short-range (e.g., less than 10 m) medium data rate (e.g., greater than 10 Mb/s) transmission. A UWB-IR transmitter (TX) directly radiates a train of short (e.g., less than 1 ns) pulses each typically representing one symbol. The direct transmission of impulses results in high data rates as the symbol period can be nearly as small as the duration of the individual impulses. Compared with some existing low-power narrow-band transmitters, UWB-IR transmitters may offer 10 times or higher bandwidth and lower per-bit energy dissipation.

The high bandwidth of a UWB-IR TX, however, comes at the cost of reduced TX power efficiency. Compared with some existing narrow-band TXs, UWB-IR TXs may be at least 4 times less power efficient. The reduced power efficiency of the UWB-IR TX may be attributed to poor efficiency of the output stage which drives the antenna. Unlike narrow-band transmitters, which typically utilize a high-efficiency switching power amplifier (PA), a UWB-IR TX that derives the data signal from the power signal cannot typically use a switching PA since the main component of the typical switching PA, a passive narrow band filter, would block the UWB impulses entirely.

In some low-power UWB-IR architectures, a set of inverters generates the UWB waveform and drives the antenna. In these architectures, the TX only radiates power during the logic-state transitions. The TX efficiency is therefore limited by that of a CMOS inverter during rise and fall times which is limited to 50% in the ideal case. In practice, due to the added consumption in the digital delay-lines and other pulse-shaping circuits, the architecture tends to yield a small overall power efficiency of approximately 0.5%.

The circuit of FIG. 4(a) generates UWB pulses by activating a switch (400) to turn on and off a digitally-controlled cross-coupled LC tank (402) which operates as an oscillator. In this circuit, the TX efficiency performance therefore depends on the efficiency of the LC tank (402) during the startup period. Power efficiency slowly increases to its maximum value in the steady state. Generally, the pulse period is over prior to the steady state and the LC tank (402) is switched off.

In the circuit of FIG. 4(b), a low power UWB data transmission is provided by obtaining pulses from the power coil, shaping them with a diode-pair, then feeding them into a UWB antenna. The inclusion of the diode-pair effectively keeps the high-speed RF path outside of the sensors/tag chip semiconductor region of the device where the electronics are typically much slower than the passive substrates of the coil, antenna and the feedlines outside the chip. Using this technique, an RFID tag, wireless sensor or a wireless medical implant can send out many times more data using a small power budget at the minimal cost of adding the diode-pair between the power harvesting coil and the data transmitting antenna. Moreover, using this architecture, a wireless sensor or biomedical implantable or wearable device will have more power available to provide to its functional circuitry to increase sensing resolution, speed or accuracy, or to and/or to decrease frequency of maintenance for battery replacement, etc. In the case of wearable and implantable biomedical devices, the devices can sense and transmit many times more data at much faster pace than the aforementioned available wireless interface systems.

In this circuit, the UWB pulses are generated from an LC tank (404) oscillating in the steady state, such that the high efficiency of the resonant LC tank (404) can be maintained. The LC tank (404) is permitted to remain in the steady state and two UWB pulses (406) are generated in every oscillation period. The high-bandwidth pulses (406) are generated by clipping the output of the LC tank (404), V2 (408), with two diodes (410) between two DC levels (0V 412 and VMAX 414). The clipped signal, V2 (408), contains higher-order harmonics due to the abrupt limiting action of the diodes (410). The spectral power of the higher order harmonics depends on the threshold voltages VMAX (414) and VMID (shown in FIG. 7) which are digitally controlled with DAC1 and DAC2 (shown in FIG. 7). A raw UWB pulsetrain, V3 (406), is created at the antenna (416) by high-passing the clipped signal V2 (408). In an example implementation, it has been found that a circuit conforming to this UWB-IR TX provides an overall power efficiency of about 21.3% at a data rate of about 230 Mb/s.

Therefore, it will be appreciated that the present system is operable to provide a very high datarate even in view of potential reduction of power efficiency. Thus, the system provides a suitable approach to enabling high data rate wireless power and data communication with wearable and implantable devices, while permitting designers of such devices to mitigate power efficiency to meet safety needs. The following provides further aspects of the system.

Figure 5:
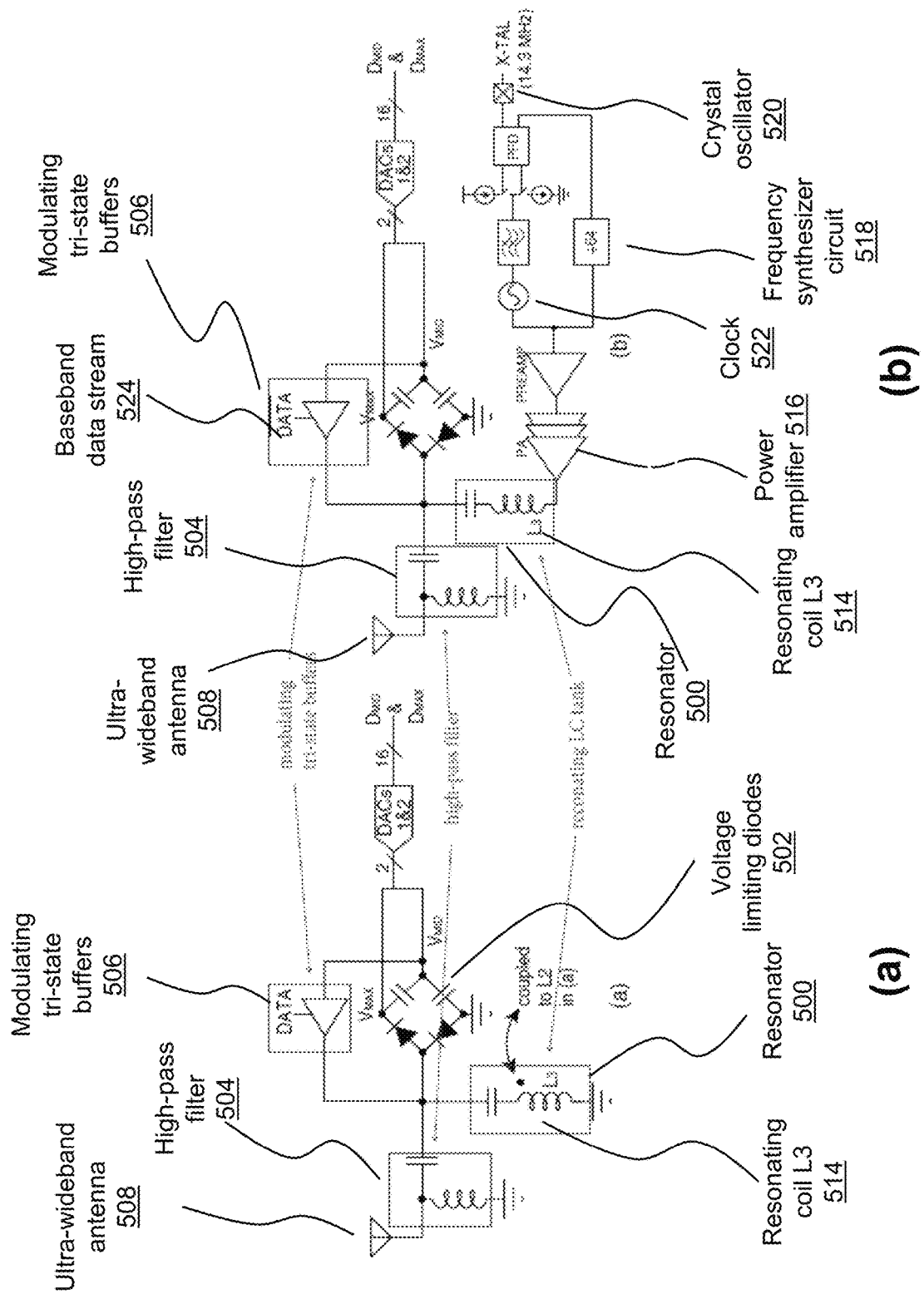
FIG. 5 illustrates an exemplary schematic diagram of a UWB pulse radio transmitter circuit.

Referring now to FIG. 5, two examples of a pulse radio data transmitter are shown. FIG. 5(a) is a schematic diagram of a pulse radio data transmitter including a resonator (500) implemented as a resonating LC tank, voltage limiting diodes (502), high-pass filter (504) modulating tri-state-buffers (506), and ultra-wideband antenna (508). The radio data transmitter is powered by the inductive power receiving circuit and uses another resonant coil, L3 (512), which is closely coupled to the power receiving coil L2 (shown in FIG. 3). The resonating coil L3 (512) creates a high voltage sinusoidal swing which when limited by the diode-cap bridge, results in sudden short pulses being ejected in to the feedline of the UWB antenna.

FIG. 5(b) is a schematic diagram of a variation of the circuit of FIG. 5(a), embodied as a standalone radio transmitter (i.e., without the inductive powering). In absence of the inductive receiving coil L2, the resonating coil L3 (514) is driven by a separate power amplifier (516) which boosts the output of a frequency synthesizer circuit (518) which generates, for example, a pure 915 MHz frequency tone from a 14.3 MHz crystal oscillator (520) as a reference. The clock (522) to run the sensors is also sourced from the crystal oscillator (520) so that the baseband data stream (DATA) (524) is in synchrony with the UWB pulse train.

Figure 6:
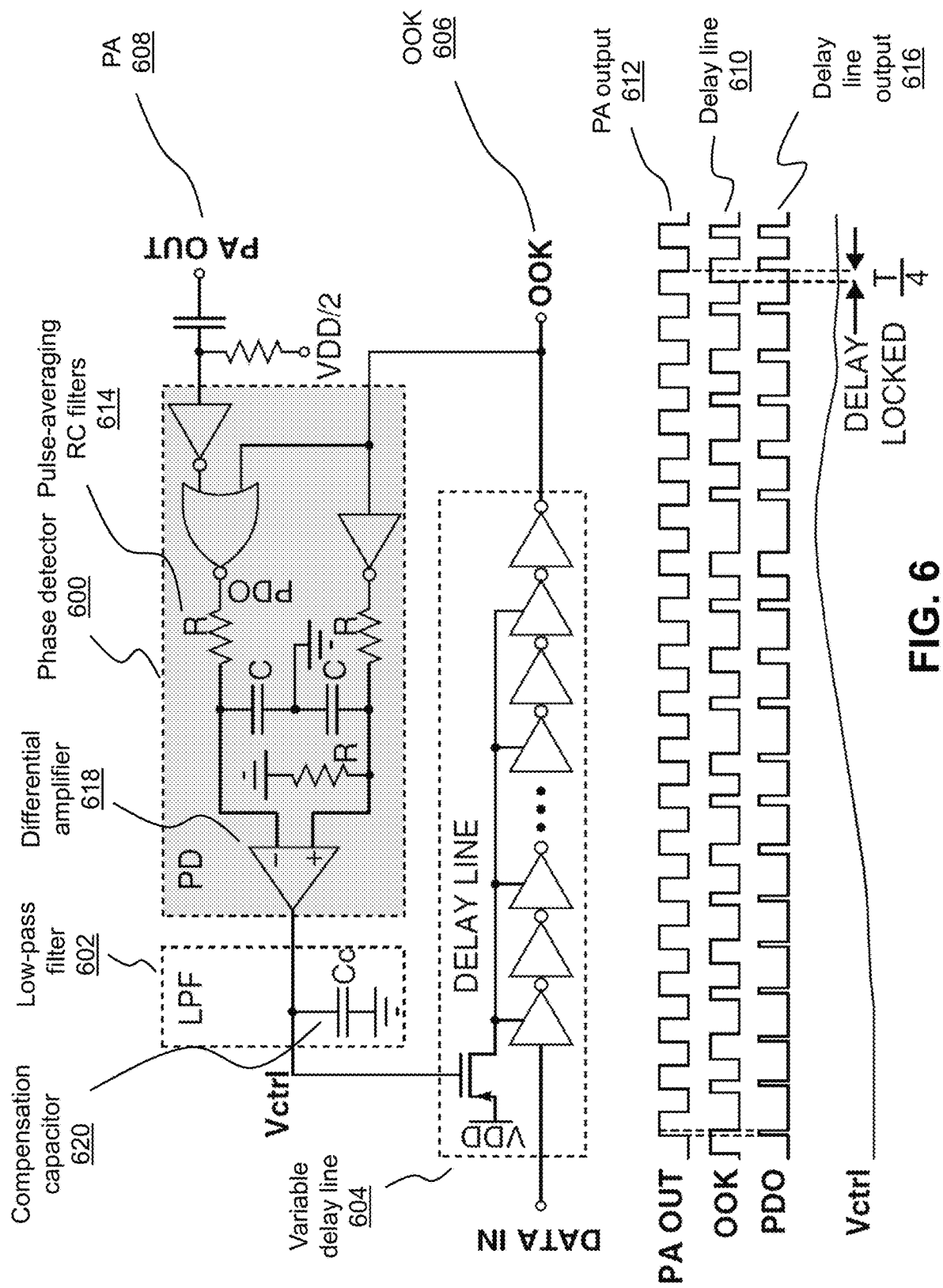
FIG. 6 illustrates an exemplary schematic diagram of a DLL circuit used for OOK modulation.

A delay-locked-loop (DLL), an example of which is shown in FIG. 6, may be used to align the baseband data stream bits with the UWB pulse train. The DLL comprises a phase detector (PD) (600), low-pass filter (LPF) (602), and variable delay line (604). The DLL regulates the variable delay of the inverter-chain delay line until the outputs (610, 612, respectively) of the delay line (the on-off key, OOK) (606) and the PA (608) are misaligned by exactly T/4, where T is the LC tank oscillation period, and with the latter rising edge preceding.

The DLL quantifies the misalignment between the two rising edges by comparing the duration of every OOK "1" bit with the duration of the concurring "1" bit of the output of the PA being positive. For this, the PA output (612) is digitized to a squarewave using an inverter with an AC-coupled input, as shown in FIG. 6. The digitized PA output is NORed with the output of the delay line (610). Two pulse-averaging RC filters (614) quantify the pulsewidths of the data "1" bits as seen at the output of the delay line (610) and the output bits NORed with the PA output (612). The RC filter which averages the delay line output (OOK) (616), as shown in FIG. 6, has a DC gain of ½, such that the two filters output may be at equal levels when the PA and the data bits are exactly a quarter of a period apart in phase. The difference between the outputs of the two RC filters is quantified by a differential amplifier (618) which may be implemented as a self-biased differential pair. The compensation capacitor Cc (620) may be added to the differential amplifier output to stabilize the feedback loop. As shown in the timing diagram of FIG. 6, an auxiliary quarter-period "1" bit may follow every data bit to ensure that the loop settles only when the bits precede the PA zero crossings by a T/4. Without the auxiliary "1" bit, the DLL may just as likely settle when the bits follow the PA output by a T/4.

Figure 7:
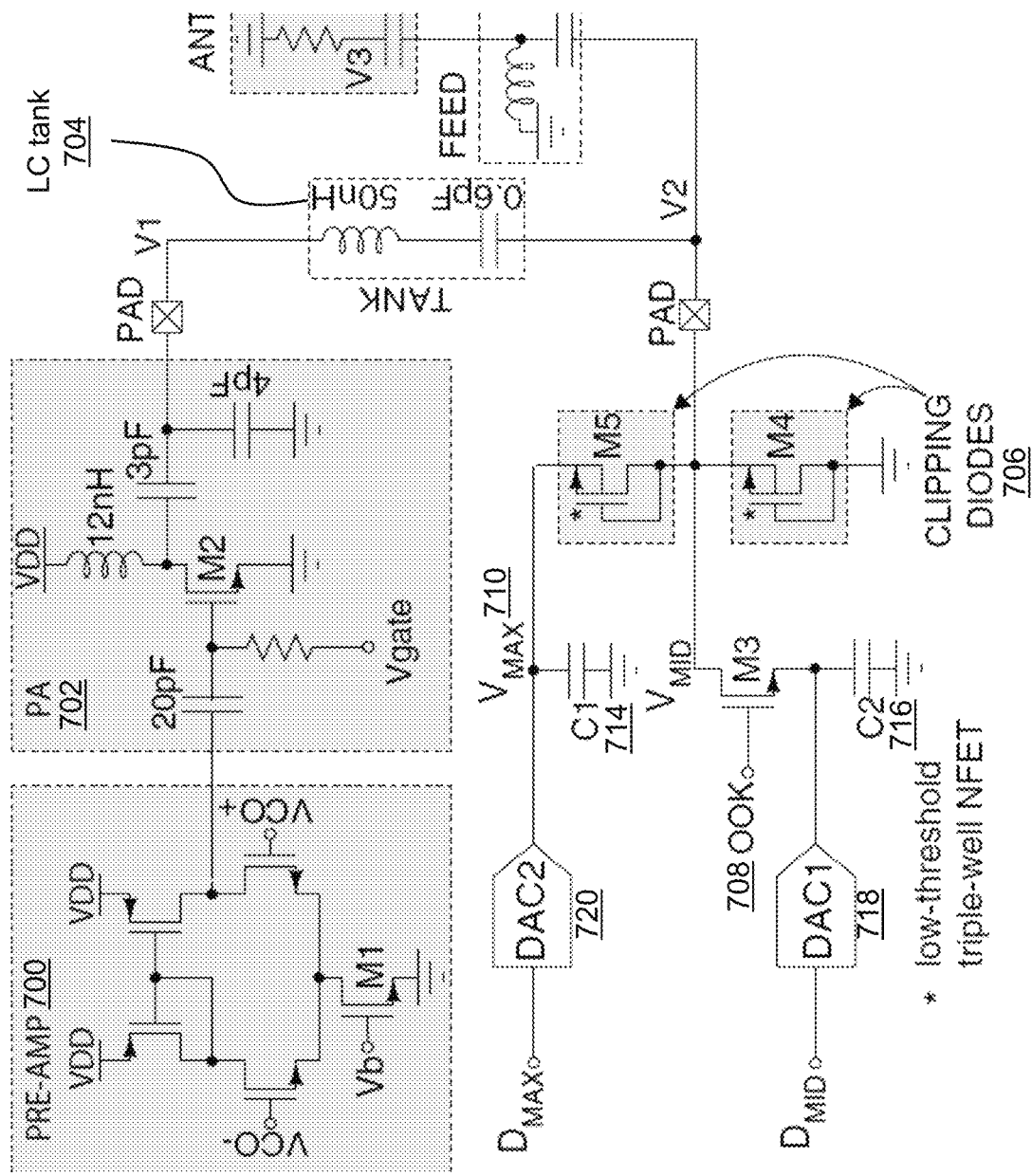
FIG. 7 illustrates an exemplary transistor-level schematic of a UWB pulse generator.

FIG. 7 shows a schematic diagram of a pulse generation circuit comprising a pre-amplifier (700), power amplifier (702), LC tank (704), clipping diodes (706) and OOK switch (708). The pre-amplifier shown is a self-biased differential pair with current mirror biasing for the tail current device M1. The power amplifier shown is a common-source stage with an inductive load biased as a class-C amplifier. Low-frequency components of the TX output waveform are further suppressed by the high-pass characteristics of the antenna feedline.

The clipping diodes shown are each implemented by two series diode-connected triple-well NFET devices (M4, M5). In an example embodiment, all the diode-connected devices have a width of 50 μm and the minimum length possible. The OOK switch may be implemented by the NMOS device M3 which may be characterized by the minimum length and a width of 200 μm. To set the DC threshold voltages VMAX (710) and VMID (712), C1 (714) and C2 (716) may be used as decoupling capacitors at the outputs of DAC1 (718) and DAC2 (720). C1 and C2 may, for example, be implemented with banks of poly capacitors each, for example, with the total capacitance of 200 pF.

Figure 8:
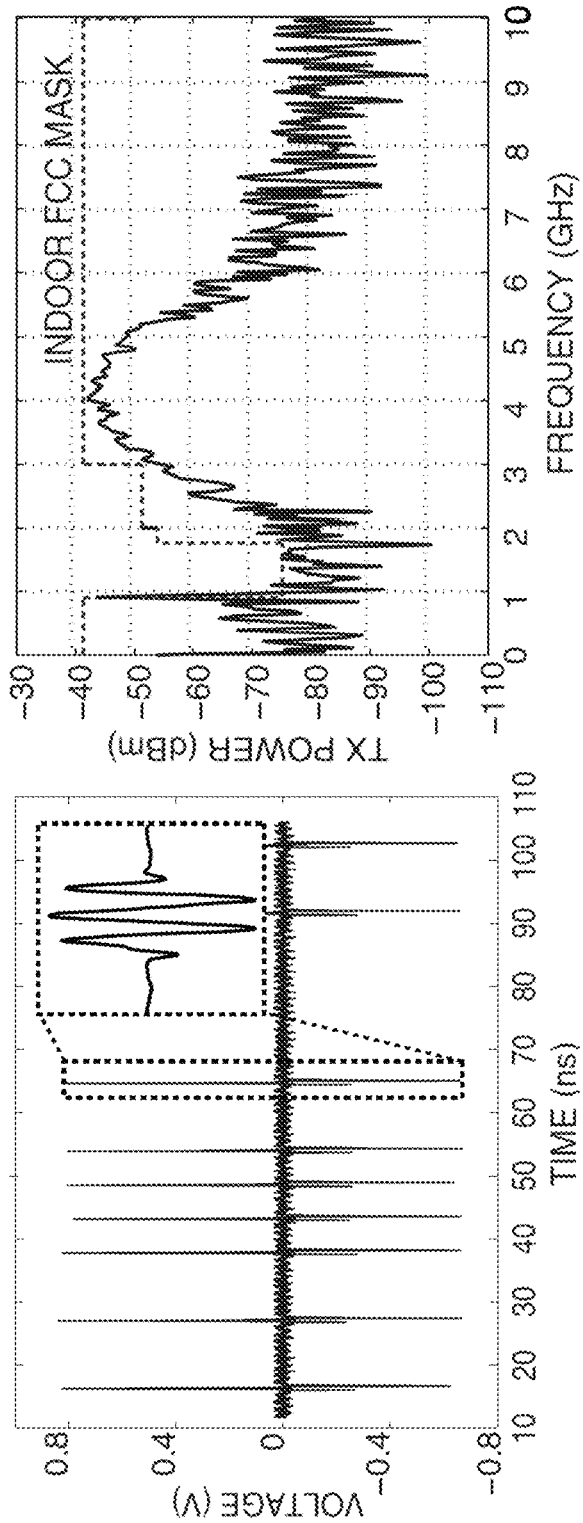
FIG. 8 illustrates an exemplary modulated time-domain output of a transmitter and power spectrum.

FIG. 8 illustrates a signal output representing an example modulated transient output of the transmitter at the maximum output power. FIG. 8(*a*) shows the transient output of the transmitter modulated by a pseudorandom binary sequence (PRBS). FIG. 8(*b*) is the spectrum of the OOK modulated pulse train spread over the 3-5 GHz frequency range. At higher UWB frequencies, antennas typically either have a small aperture or are extremely sensitive to misalignment. Therefore extending radiated spectral power beyond this frequency range may be of less interest, especially for biomedical wearable and implantable sensor applications where misalignment of antennas often cannot be avoided.

Figure 9:
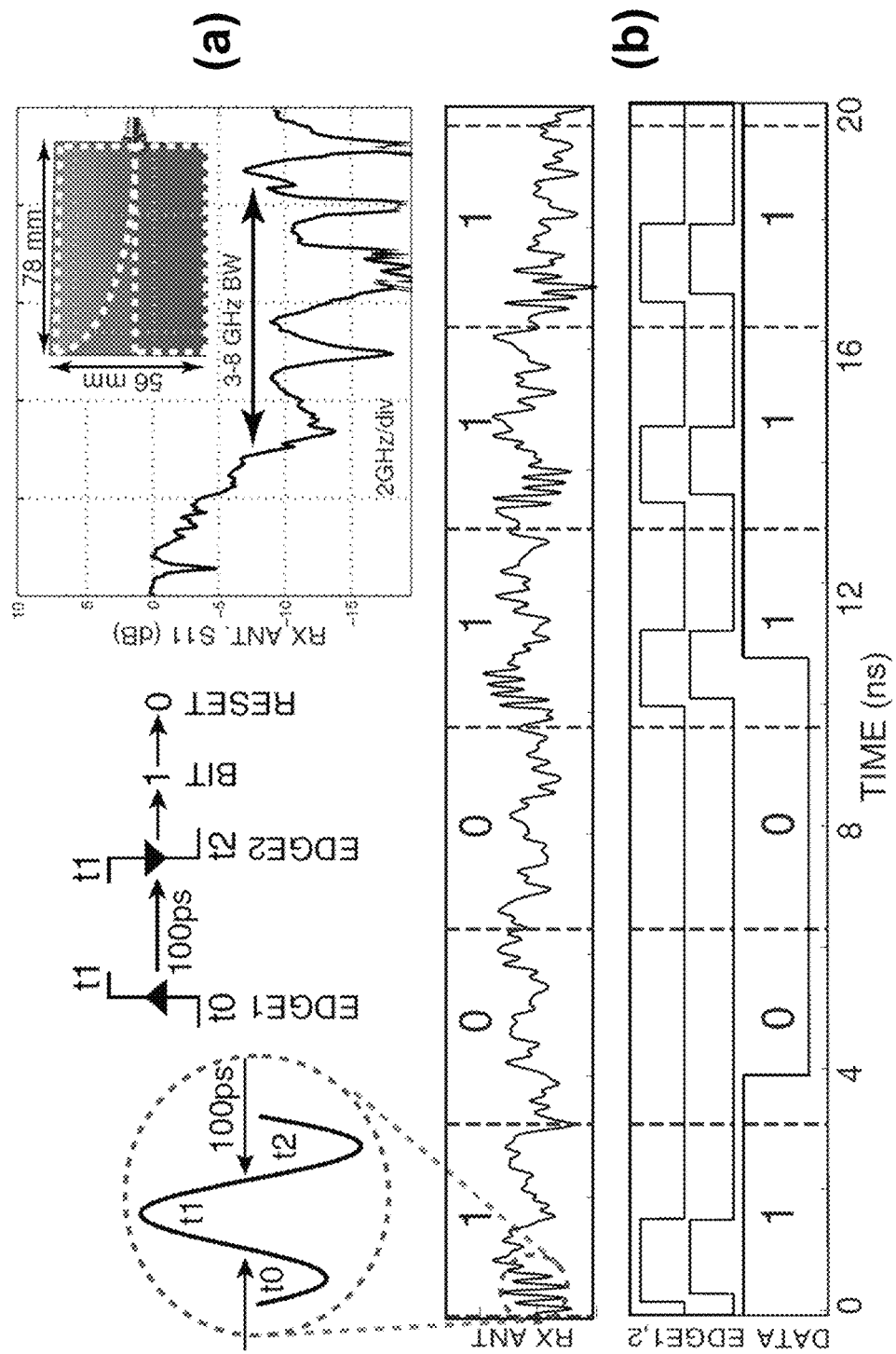
FIG. 9 illustrates an exemplary receiving antenna return loss and measured output.

FIG. 9 illustrates a signal output representing transmitted pulses. A receiver recovers the pulses by interpreting the results according to the correlated double sampling scheme described in FIG. 9(*a*) and described below. The receiver may be set to be triggered by any notch in the received signal that is smaller than a predetermined width, such as 500 ps wide, for example. The receiver may be configured such that once a notch is detected, a segment, such as 10 ns in this example, of the recorded RX signal containing the notch is stored in a memory. All the stored RX segments may be later processed by a computer to determine the bit error rate (BER), which is determinable following determination of bit value. The computer may perform a correlated double sampling scheme as shown in FIG. 9(*a*). By taking three consecutive samples from the RX signal in predetermined intervals, such as 100 ps in this example, the computer may detect whether a transmitted UWB pulse exists within each stored segment of the scope. The "EDGE1" and "EDGE2" signals are the outputs of two slope detection blocks within the scheme which evaluate the rise in amplitude from t0 to t1, and from t1 to t2, respectively. A UWB pulse may be flagged to be present within the segment when the output of both slope detectors "EDGE1" and "EDGE2" are high. A bit "1" may be assigned to each recorded RX segment when the algorithm detects a UWB pulse during that segment. Each segment may also have a time stamp recorded therein using a separate channel. By comparing the bit "1" segments with the original transmitted PRBS sequence, the BER may be estimated. A bit "0" may be assumed where no pulse is detected by the algorithm. FIG. 9(*b*) shows the combined output of the two detectors based on the detection scheme in FIG. 9(*a*). FIG. 9(*a*) also illustrates a receiving UWB antenna, and its return loss plot over the 0-10 GHz frequency range, which shows that it may be most sensitive to signals within the 3 GHz-8 GHz frequency range.

Figure 10:
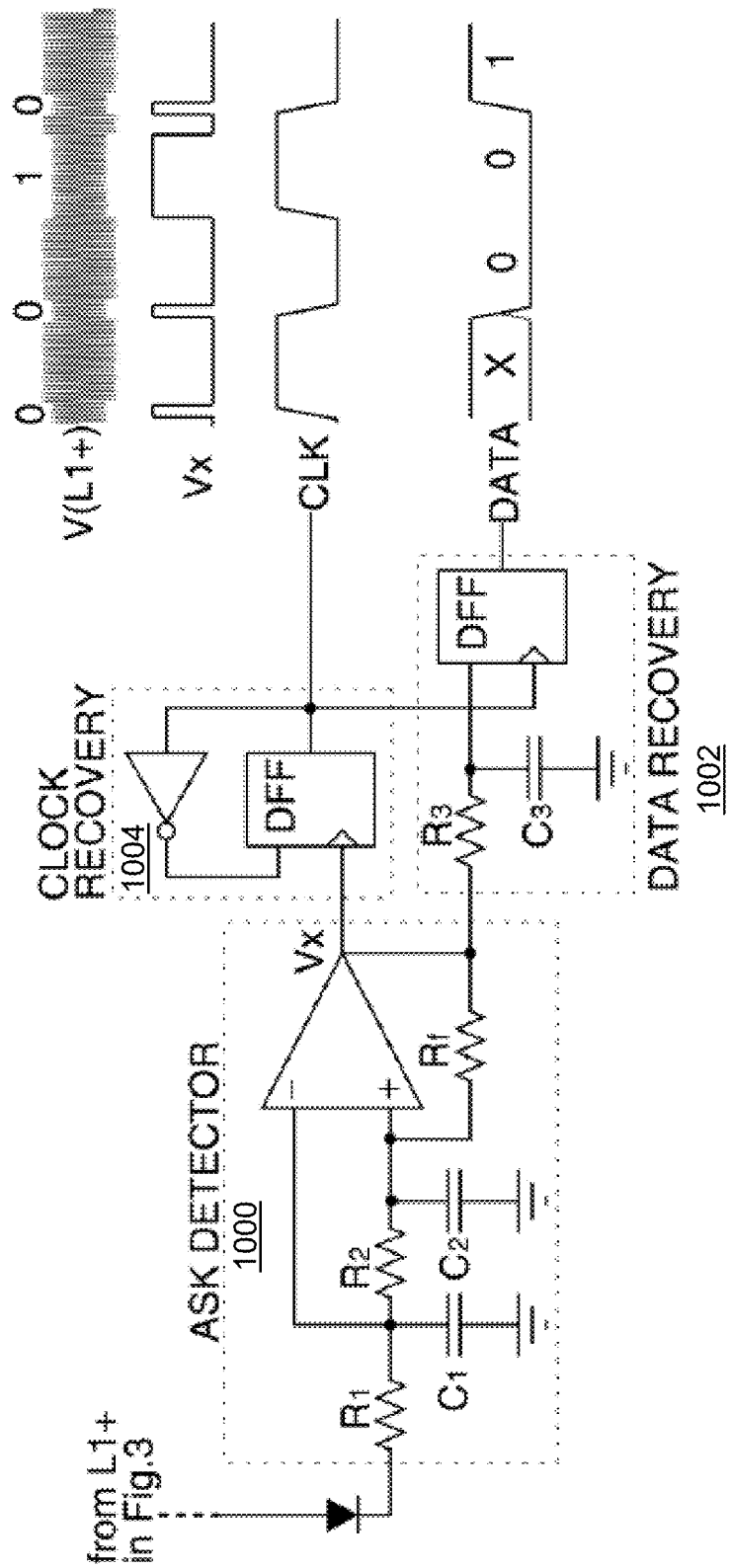
FIG. 10 illustrates an exemplary schematic diagram of a near-field data receiver.

Referring now to FIG. 10, the system may further comprise a near-field data receiver for command transfer. The near-field data receiver may comprise a digital envelope detector (1000), a data slicer (1002), and a clock recovery circuit (1004). The data recovered by the receiver may be used to configure the sensors or activate all or a subset of the actuators. A PWM envelope containing both clock and data information may be sourced from the power receiving coil L2 (as seen in FIG. 3). To communicate with the receiver, short intervals of attenuation in the envelope, V(L1+), may denote "0" bits while a long gap may denote "1's". Regardless of whether a 0 or 1 is being received, the voltage Vx may rise which may cause the clock output (CLK) to toggle at fixed intervals. The data bits may then be recovered at each edge of the clock based on the length of the last pulse in Vx.

Figure 12:
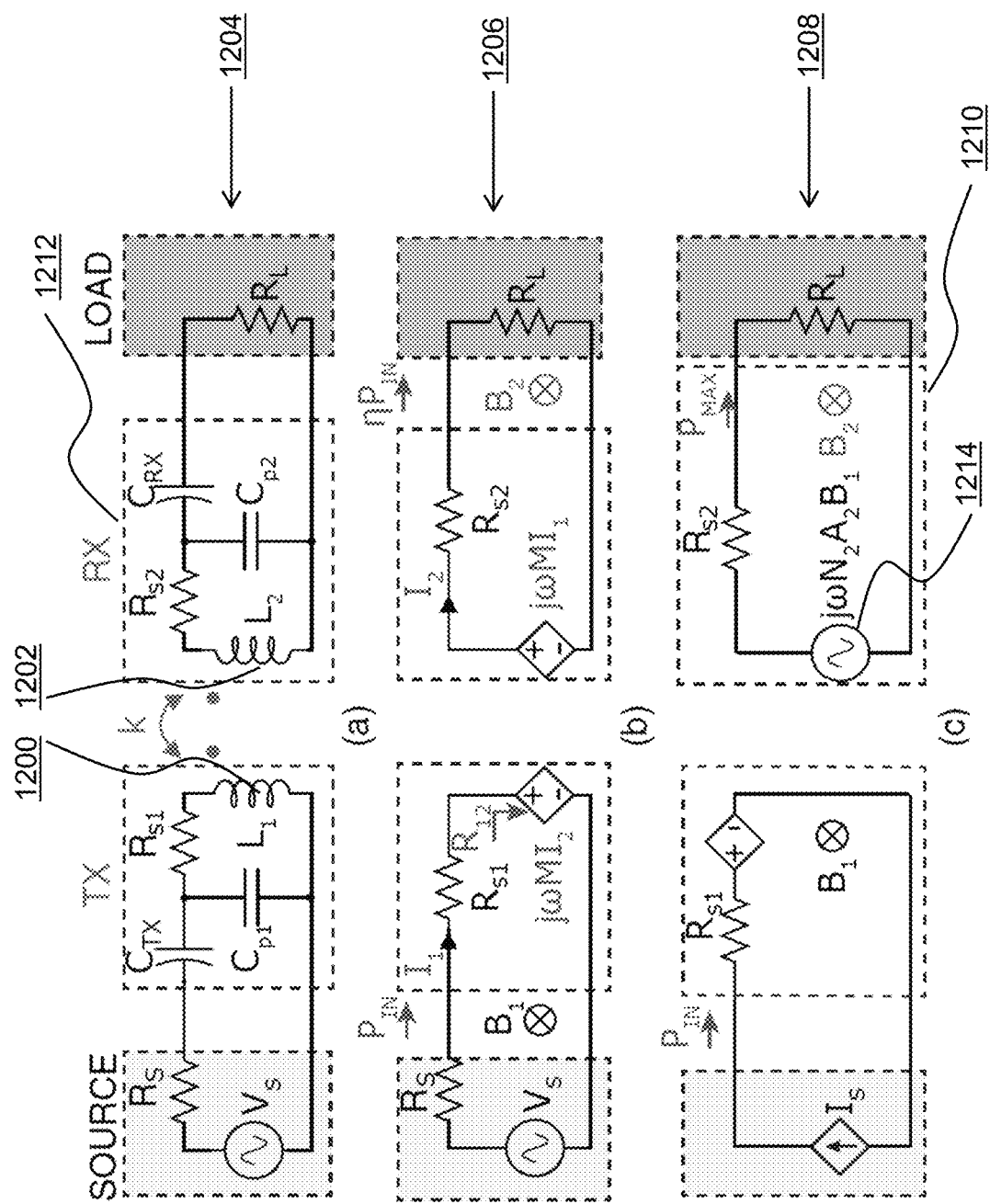
FIG. 12 illustrates exemplary circuit models of an inductive powering system.

In another aspect, and referring to FIG. 12, a set of resonant inductive coils (1200, 1202) being optimized for maximum SAR-constrained power transfer (PLmax) is provided. A method comprises optimizing the geometries of magnetic coils comprising maximizing a coil fill factor and a number of turns until the fraction power lost in a biological medium is minimized.

Figure 11:
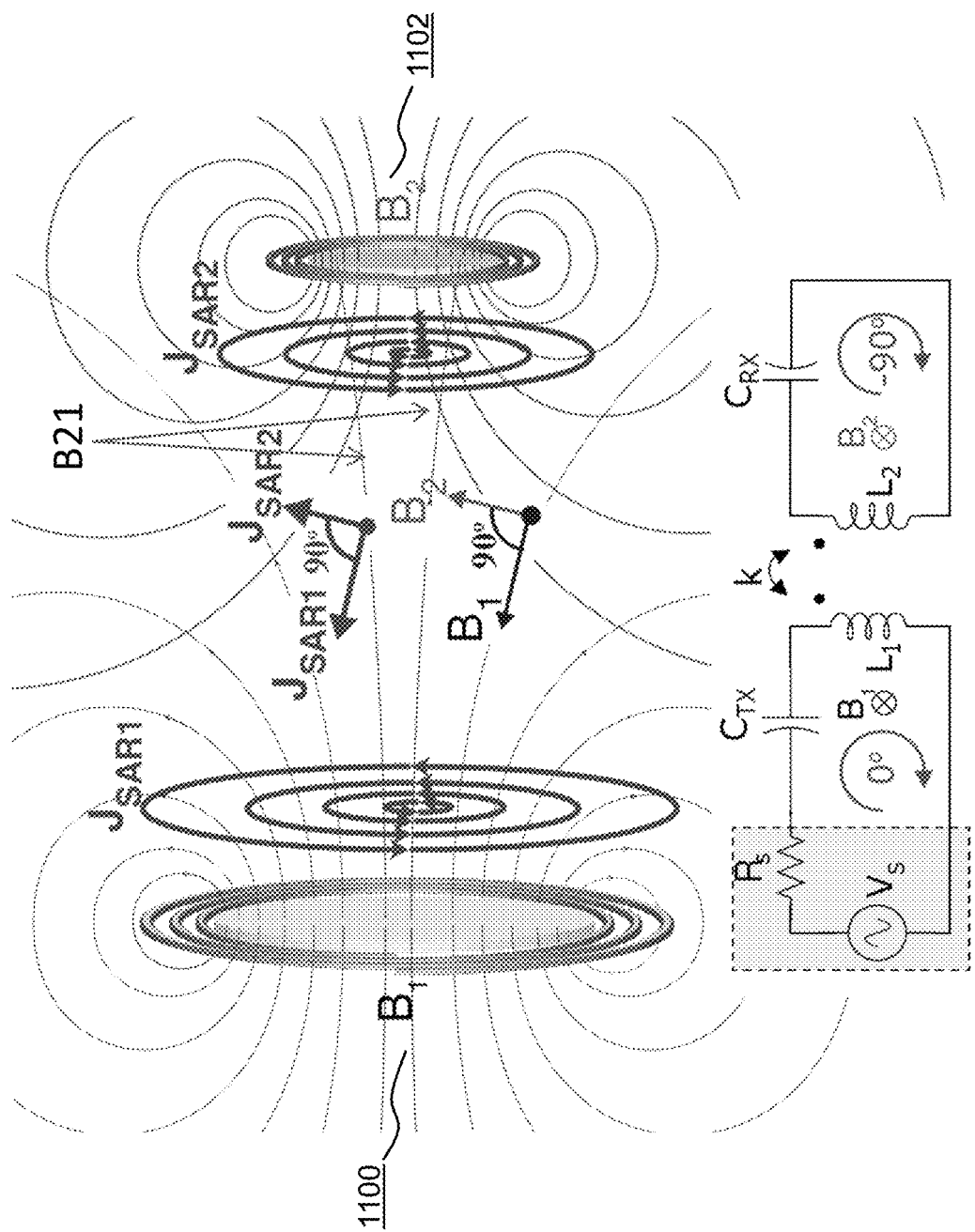
FIG. 11 illustrates orthogonal-phase dissipative currents induced in biological tissue by coupled resonant coils.

FIG. 12(*a*) shows the lumped model (1204) of the resonating 2-coil system in FIG. 11. FIG. 12(*b*) shows an equivalent simplified circuit (1206) to FIG. 12(*a*). FIG. 12(*c*) shows an equivalent simplified circuit (1208) to FIG. 12(*b*).

At frequencies well below the self-resonant frequency (SFR) of the coil (1200, 1202), the parasitic capacitances between the coil turns may be neglected. Neglecting the parasitic capacitances, the lumped model (1204) may be simplified as shown in the 2-port model (1206) in FIG. 12(*b*). All reactive parts in this circuit (1204) are eliminated due to resonance. Based on the resonant model (1206) in FIG. 12(*b*), the SAR-constrained model (1208) of the inductive power transfer system in FIG. 12(*c*) can be derived. The magnetic flux density is strongest at the receiver (1210); therefore, the receiver current has known value in this model. Thus, the receiver (1212) may be modelled as powered by an independent source (1214) in the lumped model (1210) of FIG. 12(*c*).

As shown in FIG. 11, magnetic fields of the 2 coils, B1 (1100) and B2 (1102) resonate in orthogonal phase, and the total magnetic flux density is B2,Tot=B21+B2, assuming quality factors of both coils are high enough such that Q1^2 (square of quality factor of first coil)>>1 and Q2^2 (square of quality factor of second coil)>>1. B21 is the small component of the magnetic field at the second coil which is sourced from B1. In other words, B21 is the field of the first coil at the location of the second coil. As B2 is created by induction of B1 into L2, and assuming that size of first coil is bigger that the gap between the coils, total local flux density at the receiver may be approximated by:

$$B_{loc}^2 \approx B_1^2(1+Q_2^2) \quad (1)$$

Figure 13:
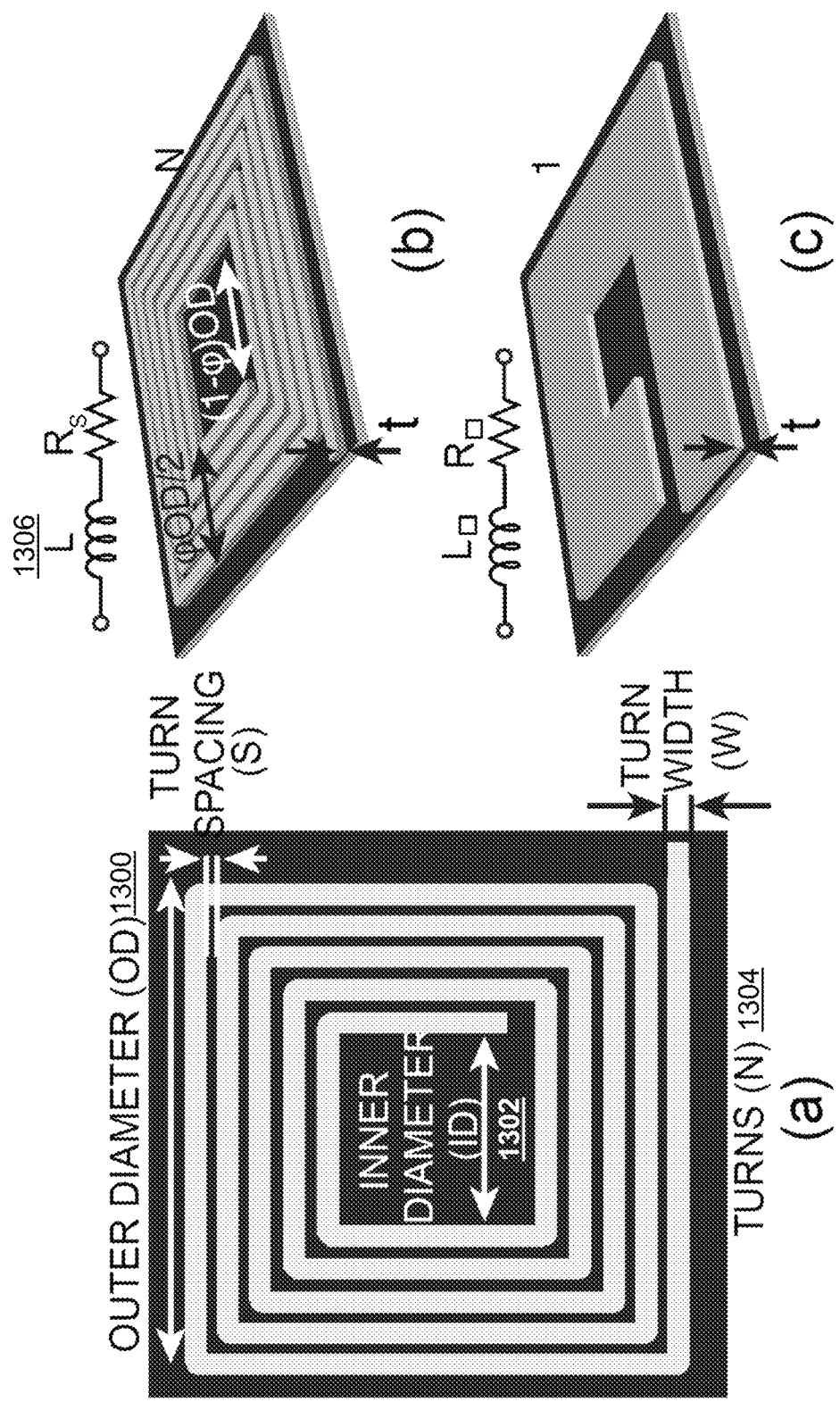
FIG. 13 illustrates an exemplary layout of a square spiral inductor developed on a 2-layer printed circuit board.

Therefore, the loaded quality factor of the second coil, $Q_2$, can sharply increase local SAR and reduce the maximum deliverable power. FIG. 12(*c*) shows the flux-constrained model of the inductive power transfer system in FIG. 12(*a*) and FIG. 12(*b*) assuming the diameter of the first coil is larger than the gap so that B1 at the second coil is not attenuated significantly. The total delivered power is then given by:

$$P_L = \left( \frac{\omega N_2 A_2}{\sqrt{R_L} + \frac{R_{s2}}{\sqrt{R_L}}} \right) \quad (2)$$

where $A_2$ is the effective area of the second coil, $R_L$ and $R_{s2}$ are load and conductor resistances and $N_2$ is number of turns, all referring to the second coil. As evident from the above equation and the half-circuit model for the second coil in FIG. 12(*c*), the delivered power to the load ($R_L$) is maximized at the upper limit of the flux density, $B_{Tot}=B_{max}$ and the load resistance of $R_L=R_{s2}$; in other words the load must be matched to the winding resistance of the second coil. Using the exposure limit of $16.3/f_M A_m-1$ and $407.5/f_M A_m-1$ for the whole body and local SAR for the frequencies between 0.1 MHz-100 MHz (where $f_M$ is the operating frequency in MHz), the absolute maximum transferable power to the load may be determined by $f_M A_m-1$ for the whole body and local SAR for the frequencies between 0.1 MHz-100 MHz (where $f_M$ is the operating frequency in MHz), absolute maximum transferable power to the load may be determined by $$P_{Lmax} = P_L \Big|_{B_{max}, R_{s2}} \frac{(\omega A_2)^2}{4R_{\square 2}} \times B_{max}^2 \quad (3a)$$

$$= 1.63^2 (2\pi)^4 \frac{A_2^2}{R_{\square 2}} \min\left\{ 1, \frac{25^2}{1+Q_2^2} \right\} \quad (3b)$$

where $A_2$ is effective area, $R_{\square 2}$ is the resistance of a wide 1-turn RX inductor as shown in FIG. 13, L is the inductance per turn such that $R_S=N_2R_\square$ and $L \approx N_2 L_\square$ ($R_\square$ is independent of size while $L_c$ is proportionate to OD) and $f_M$ is the operating frequency in Megahertz.

In the maximum power transfer equation 3b, the whole body SAR limit dominates at lower frequencies while the local SAR term dominates at high frequencies where Q22>>1. The critical frequency above which local SAR limits power transfer is $$f_{opt} \approx 2 \times \frac{R_{\square 2}}{L_{\square 2}}, \quad (4)$$

which is effectively the highest frequency that will result in maximum power delivery.

According to equation 3b, when $f_M <= f_c$, the maximum transferable power is determined by OD (size) and copper thickness (tCu), and the value drops by frequency when $f_M > f_c$. Any frequency below $f_c$ therefore provides the maximum deliverable power. However, from the power efficiency point of view, it is not desirable to decrease the operating frequency as it leads to unnecessary loss of power in the transmitter. Therefore, we conclude that $f_c$ is the optimal operating frequency for inductive power transfer systems having live human or animal tissue as medium.

Planar coil design parameters, as shown in FIG. 13(*a*), are outer diameter (OD) (1300), inner diameter (ID) (1302) and number of turns (N) (1304). The dimensions of the receiving coil are typically dictated by the size of the device. On the other hand, ID (1302) may have an optimum value. Qualitatively, reducing the ID (1302) by adding more inner turns to the inductor (1306) in FIG. 13(*b*) will increase the induced voltage but increases the winding resistance of the coil. However, the turns in the center generally do not contribute significantly to the induced voltage despite still significantly increasing the parasitic resistance. Therefore, an optimal ID (1302) may exist which maximizes PLmax.

Figure 14:
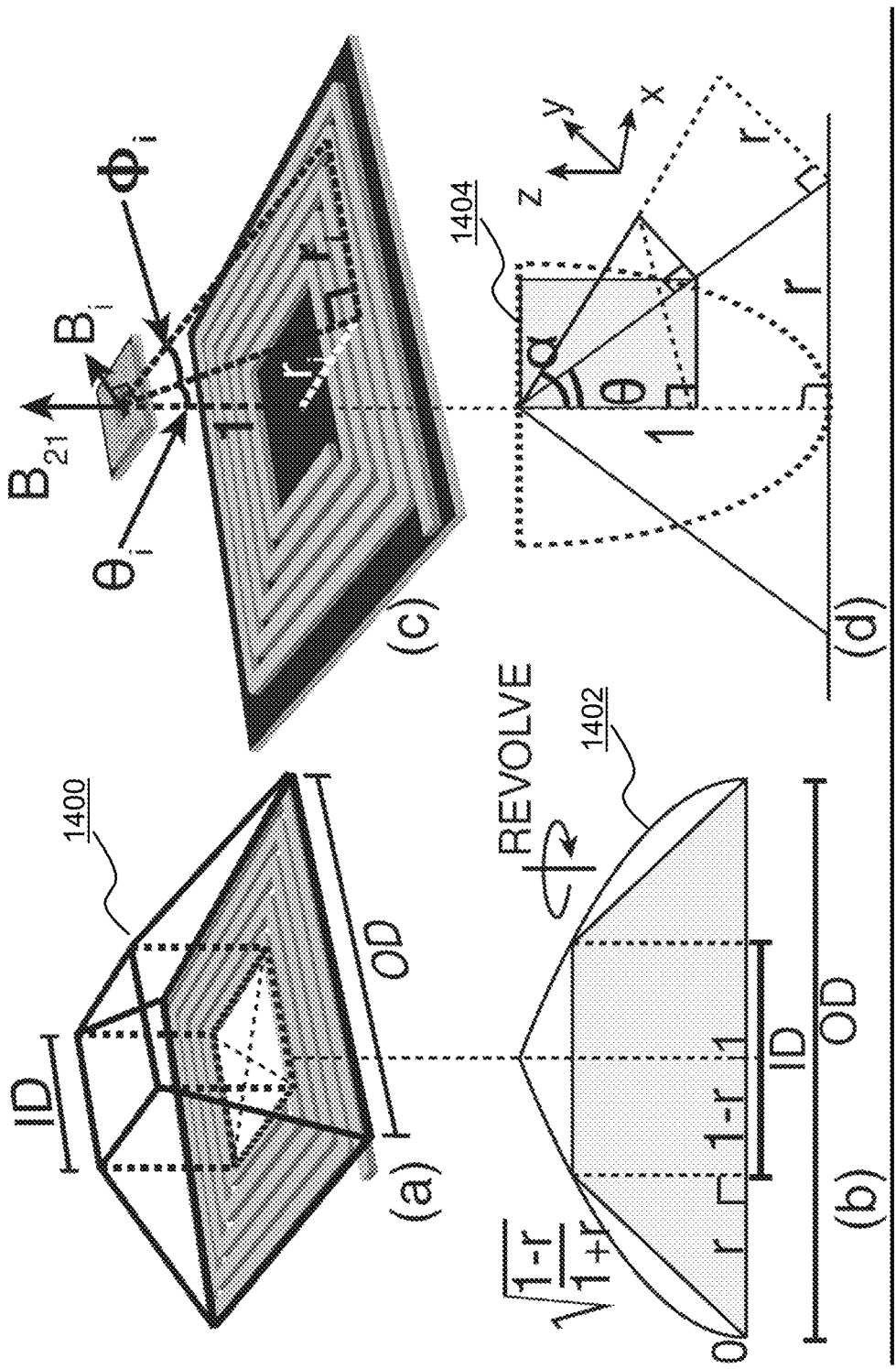
FIG. 14 illustrates exemplary inductance and quality factors of transmit and receiver coils.

Since OD2 is a known value, to find the optimal inner diameter for RX, the optimum value of r=ID2=OD2 must be determined. The optimal r maximizes PLmax for a given induced flux density $B_{21}$. FIG. 14 shows the geometrical representation of $\sqrt{PLmax}$ described by equation 3a in terms of $A_2$ and $R_{s2}$, where the volume of the 3D trapezoid (1400) in FIG. 14(*a*) is proportional to the total induced flux, and the volume under the dome (1402) in FIG. 14(*b*) which results from revolving the arcs and the trapezoid represents square root of total delivered power ($\sqrt{PLmax}$). Based on FIG. 14(*b*), there is an optimum fill factor, $\varphi opt2$, which maximizes the volume of the 3-dimensional trapezoid under the dome (1402) in FIG. 14(*b*). This volume represents the maximum transferable power to a coil with outer diameter of 1, and its value is given by:

$$P_{Lmax} = \frac{\sigma t}{2} \left( \frac{1-r}{1+r} \right)(1+r+r^2)^2 B_{21}^2 \quad (5)$$

Differentiating with respect to r and equating to zero yields the optimal value of r=0:37.

Figure 15:
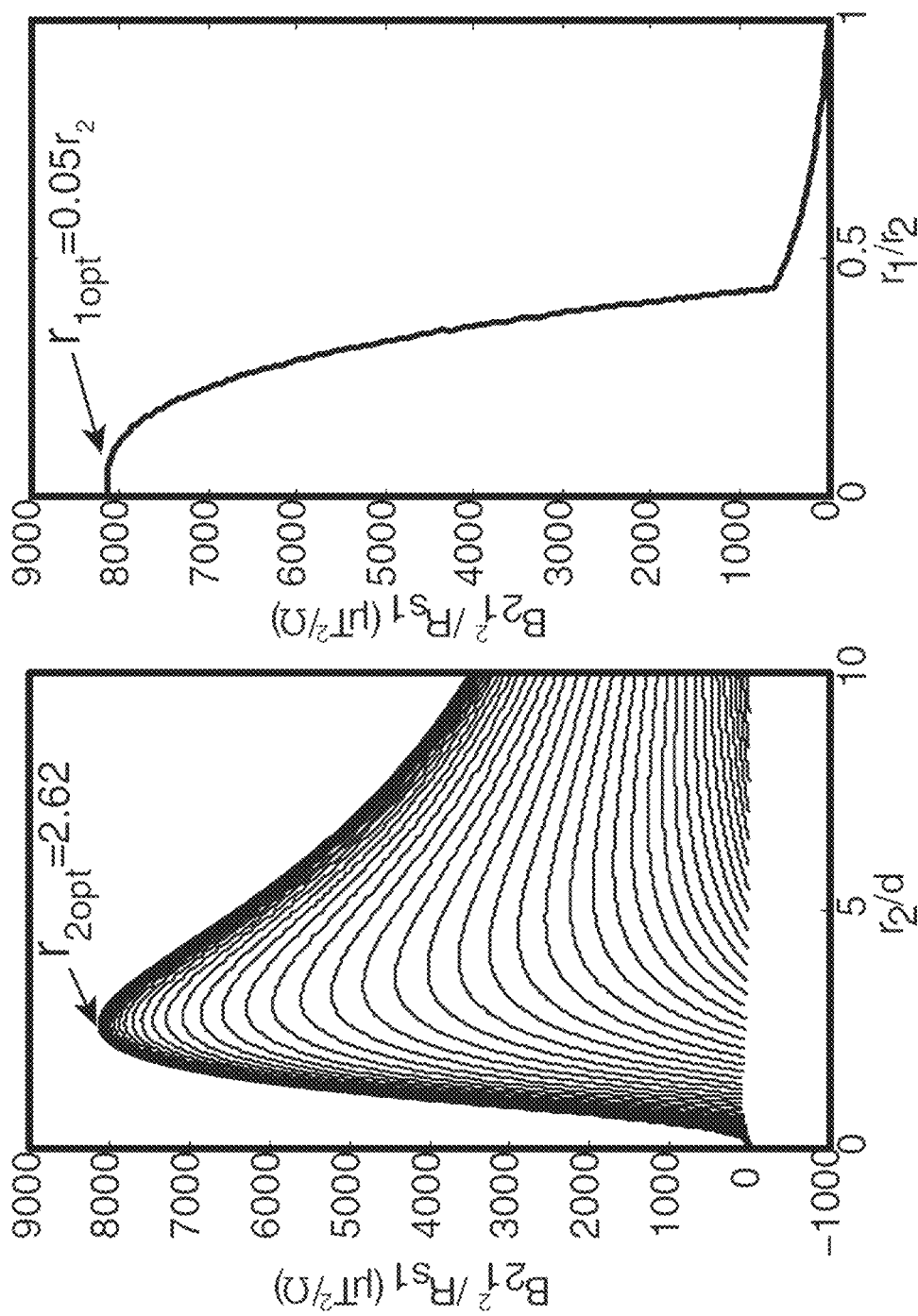
FIG. 15 illustrates SAR-optimal outer and inner radii for coils.

The size of the transmitting coil may not be limited such as in the case of the receiver. Therefore, the outer radius r1 may be where ri is the distance of the $i^{th}$ turn from the center of the coil. In the scenario where each added turn has a fixed width of w, (ri−r(i−1)=w), and assuming that w is small, the sum in equation 6 can be approximated by the definite integral $\int_{r_1}^{r_2} r^2 dr = (1+r_1 2)\sqrt{1+2r^2}$, where r1 and r2 are the inner and outer radii of the coil. Similarly, the total resistance of the coil, $R_s$, can be approximated by the definite integral $RN\int_{r_1}^{r_2} r\, dr$, where RN is the resistance of the turn at r=1. To optimize the transmitting coil is to find r1 and r2 which maximize the ratio B21=Rs1. This is equivalent to finding the roots of:

$$\frac{d}{dr_{1,2}}\left[\frac{1}{\sqrt{r_2^2 - r_1^2}} \int_{r_1}^{r_2} \frac{r^2 dr}{(1+r^2)\sqrt{1+2r^2}}\right] = 0. \quad (6)$$

which as shown in FIG. 15 has unique real roots at about $r_1=0.13$ and $r_2=2.62$, which are the optimum values of inner and outer diameters of the transmitting coil normalized to the coil separation d.

Graphically, optimizing $r_1$ and $r_2$ is to maximizing the product of cos 2θ and sin α in FIG. 14(c) and FIG. 14(d) which may be roughly represented by the shaded rectangular area (1404) when θ is small. It can be verified that disproportionately large TX coils are inefficient as cos θ and the shaded area (1404) in FIG. 14(d) tend to zero when r>>1. In practice, however, it may be beneficial to select a somewhat greater outer diameter as the coil separation d could slightly vary depending on the application. While not being the optimum size, increasing $r_2$ slightly beyond the 2.62d value may not significantly reduce the power delivery. This can be verified visually as and a in FIG. 14(d) change slowly when $r_2>2.6$.

It must be noted that this result may be valid provided the integral approximation of the sum in equation 6 holds. For instance, the approximation may not be accurate if there are only few turns in the transmitting coil which would result in the sum of equation 6 only having few terms, rendering the approximation by an integral inappropriate. On the other hand, N1 is designed to be as high as possible, making this analysis fairly accurate in such cases.

Equation 3b establishes that in the SAR-constrained model, the delivered power is a function of the size and sheet resistance of the receiving coil. Therefore, neither N1 or N2 may impact the PLmax as they do not impact the size or sheet resistance. In other words, as long as the load (RL in FIG. 12(b)) is matched to the Rs2, the receiver is at maximum power. However, the task of matching RL to Rs2 using a matching network becomes increasingly challenging when Rs2 is small. Since Rs2=N2Rs2, a practical receiving coil has as many turns as necessary to best match the RX resistance (Rs2) to the load, therefore:

$$N2 = \left\lfloor \sqrt{\frac{R_L}{R_{\square 2}}} \right\rfloor.$$

On the transmitting side shown in FIG. 12(b), both $R_{s1}$ and $R_{12}$ are proportional to N21, which again makes the coil-to-coil power delivery insensitive to N1. Here again, if N1 is small, power loss in the source resistance $R_s$ in FIG. 12(b) becomes very large, leading to poor source-to-load efficiency. Therefore, much like N2, N1 is determined by impedance matching condition. However, to minimize power loss in the TX coil, the real parts of coil impedance (in the left side network in FIG. 12(c)) must not be matched to the source resistance $R_s$, but rather much larger than RS to minimize the ohmic loss in the TX coil. On the other hand, at some point continuing to increase N1 may begin reducing the quality factor (an effect less likely to occur in the RX coil due to smaller self-resonant frequency). Based on this trade-off, the optimal number of turn for TX coil may be found as:

$$N1 = \left\lfloor \sqrt{\frac{R_S}{R_{\square 1}}} \right\rfloor,$$

where $R_S$ is the source resistance.

Optimization formulas for all coils parameters (fill factors, size and number of turns) are listed in Table I below, based on a given receiver size and maximum separation of the coils d. The formulas in Table I are based on low-frequency approximations. However, given that the optimum frequency in the analysis is also far below the self-resonant frequency, the listed expressions may be valid for SAR-constrained optimizations.

TABLE 1

COIL DESIGN FORMULAE*

| Parameter | Best PTE design | Best SAR design | Reported values |
|---|---|---|---|
| Frequency ($f_{opt}$) | $\dfrac{1/2\pi}{\sqrt{C_{pl}L_{\square 1}}}$ | $2^\dagger \times \dfrac{R_{\square 2}}{L_{\square 2}}$ | $\dfrac{\sqrt{c/k_D^{**}}}{2\pi}$ [38] |
| *Transmitting coil* | | | |
| Size (OD$_1$) | 3d | 5.24d | 3.2d [44] |
| Fill factor (φ1) | 54% | 92% | 49% [18] |
| Turns (N$_1$) | 2 | $[\sqrt{R_s/R_{\square 1}}]$ | — |
| *Receiving coil* | | | |
| Fill factor (φ2) | 46% | 46% | 49% [18] |
| Turns (N$_2$) | $\left[\dfrac{1}{\omega\sqrt{C_{p2}L_{\square 2}}}\right]$ | $[\sqrt{R_s/R_{\square 2}}]$ | — |

*For given RX size (OD$_2$) and coil separation (d)
†Based on the limit of local exposure being 1/25 that of the whole body as in [11].
**A constant in Debye relaxation model.

TABLE 11

COMMON SHEET EXPRESSIONS*

| $R_{\square 1,2}$ | $L_{\square 1,2}$ | $L_{1,2}$ | $Q_{c1,c2}$ |
|---|---|---|---|
| $\dfrac{2k_\delta}{\varphi_{1,2}\sigma t_{1,2}}$ | $\dfrac{1.27\mu_0 O\, D_{1,2}g(\varphi_{1,2})}{1+\varphi_{1,2}}$ | $N_{1,2}^2 L_{\square 1,2}$ | $2\pi f_{opt}\dfrac{L_{\square 1,2}}{R_{\square 1,2}}$ |

*where $t_{1,2}$, and σ are thickness and conductivity of metal traces, $k_\delta = t/(\delta(1 - \exp - t/\delta))$ [27] and $g(\varphi) = \left[\dfrac{\ln 2.07}{\varphi} + 0.18\varphi + 0.13\varphi^2\right]$ [9].

Table I lists the design formulae for planar square coils having the best SAR and PTE performance under 2 conditions: (a) the receiver size OD2 and distance d are constants whose value is determined by the application, and (b) the RX coil is implanted in biological tissue or worn directly on the surface of the skin, and (c) the profile of the maximum allowable SAR decreases proportionally with frequency.

The design values resulting from PLmax optimization is a unique value set of values. These value are distinct from the PTE maximization results with the exception of RX fill factor φ2.

Figure 16:
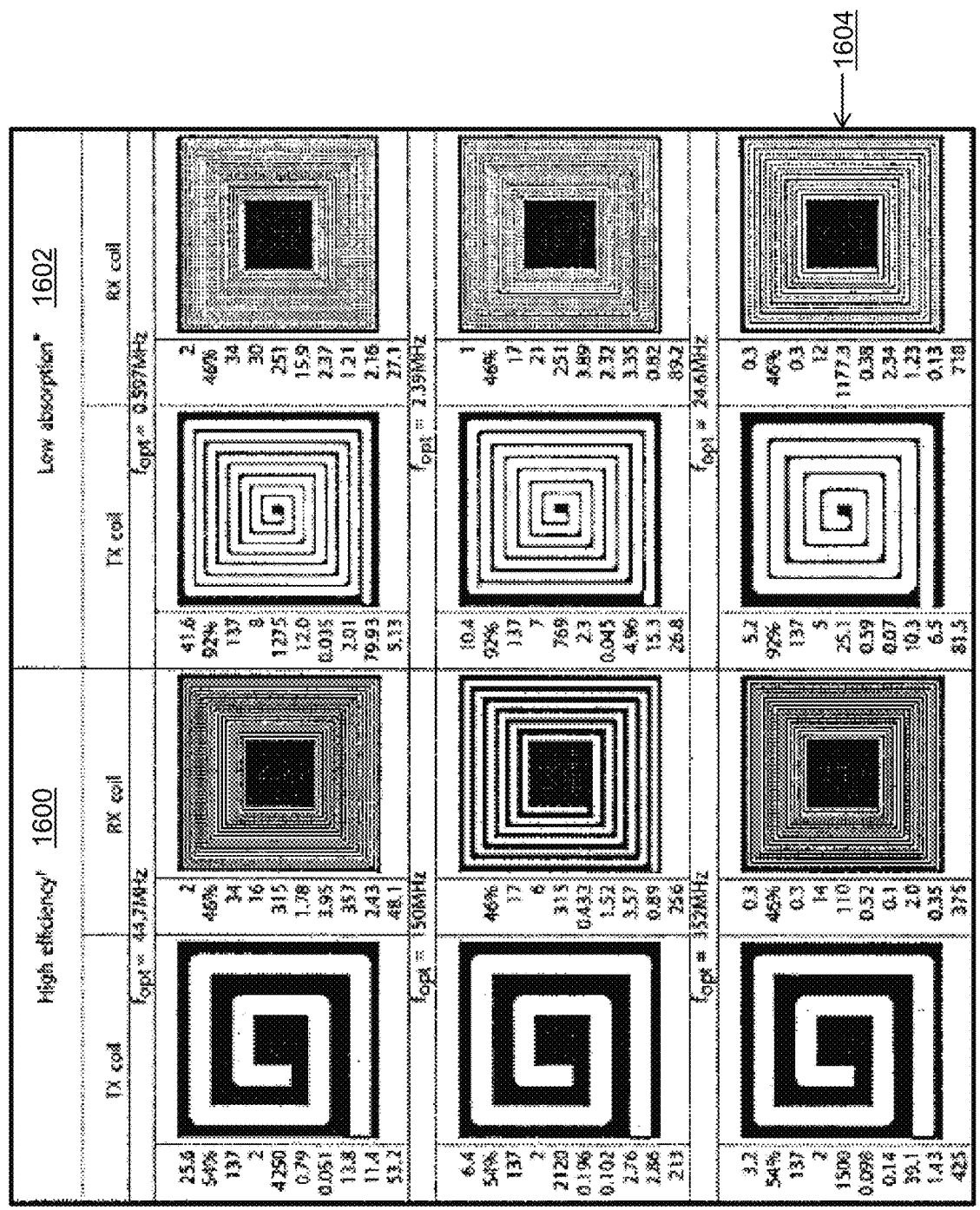
FIG. 16 illustrates exemplary coil dimensions.

FIG. 16 shows illustrative coil geometries resulting from PTE and SAR (PLmax) optimizations. The PLmax optimization results are listed in FIG. 16. It is evident that TX coils have clearly distinct shapes when designed for PLmax (1600) as compared to when designed for maximum efficiency regardless of tissue absorption (1602). The TX shape in the latter case (1602) is a full planar coil with varying number while the former (1600) is always a sparse 2-turn coil. The RX coils, on the hand, are similar in both methods, where the primary difference is their number of turns which is based on the distinct output impedance of the transmitting coils.

In the case of the 3 mm integrated inductor (third design case, 1604) in FIG. 16, both optimization analyses assume that there is no impact from the substrate under the inductor. Therefore, the analyses discount the impact of the conduction within the silicon substrate as well as its impact in reducing the self-resonant frequency of the coil. These additional effects are likely to reduce the optimum operating frequency well below values listed in FIG. 16.

The most significant distinction between the two methods, however, is the operating frequencies. The PTE favors operating at higher MHz frequencies where quality factors are maximal. This is while the optimal SAR-based design operates at the frequency where the local magnetic flux density at the RX has not increases more than 25 times that of the TX. As shown previously in sections III-B and III-C, this limits the quality factor of the RX coil which in turn limits the operating frequency to a small fraction of the self-resonant frequency. Operating at frequencies well below the SRF has other advantages such as a predictable resonance frequency value, which simplifies the design of the matching and rectification circuits.

Table IV, below, lists the operating frequencies, coil geometries and best performance metric for the inductive links reported in the three designs discussed above. The geometric and performance parameters for the designs after applying the optimization formulae in Table I is listed in bold for each design. It can be seen that despite the moderate power transfer efficiency values of 12%-28%, the designs offer an improvement of 8× to 560× in the maximum transferable power. When PLmax is well above the minimum required level to run the device attached to the RX coil, the remaining PLmax margin translates into reduced SAR level proportionate to the PLmax margin.

TABLE IV

PERFORMANCE COMPARISON

| Param. | $f_o$ (MHz) | d (cm) | $OD_1$ (cm) | $OD_2$ (cm) | $\varphi_1$ | $\varphi_2$ | $N_1$ | $N_2$ | $n_m$ (%) | $P_{Lm}$ (mW) |
|---|---|---|---|---|---|---|---|---|---|---|
| [4] | 13.6 | 1 | 4.3 | 1 | 0.77 | 0.4 | 15 | 6 | 100 | 0.5 |
| SAR-Optimized | 1.71 | 1 | 5.2 | 1 | 0.92 | 0.46 | 21 | 25 | 28 | 4 |
| [2] | 0.137 | 7 | 17 | 2.5 | 0.006 | 0.016 | 1 | 2 | 68 | 1 |
| SAR-Optimized | 13.6 | 7 | 36.4 | 2.5 | 0.92 | 0.46 | 36 | 58 | 23 | 410 |
| [5] | 13 | 4 | 13.5 | 4.4 | 0.48 | 0.023 | 3 | 3 | 77 | 10 |
| SAR-Optimized | 0.1 | 4 | 20.8 | 4.4 | 0.92 | 0.46 | 21 | 112 | 12 | 5600 |

Figure 17:
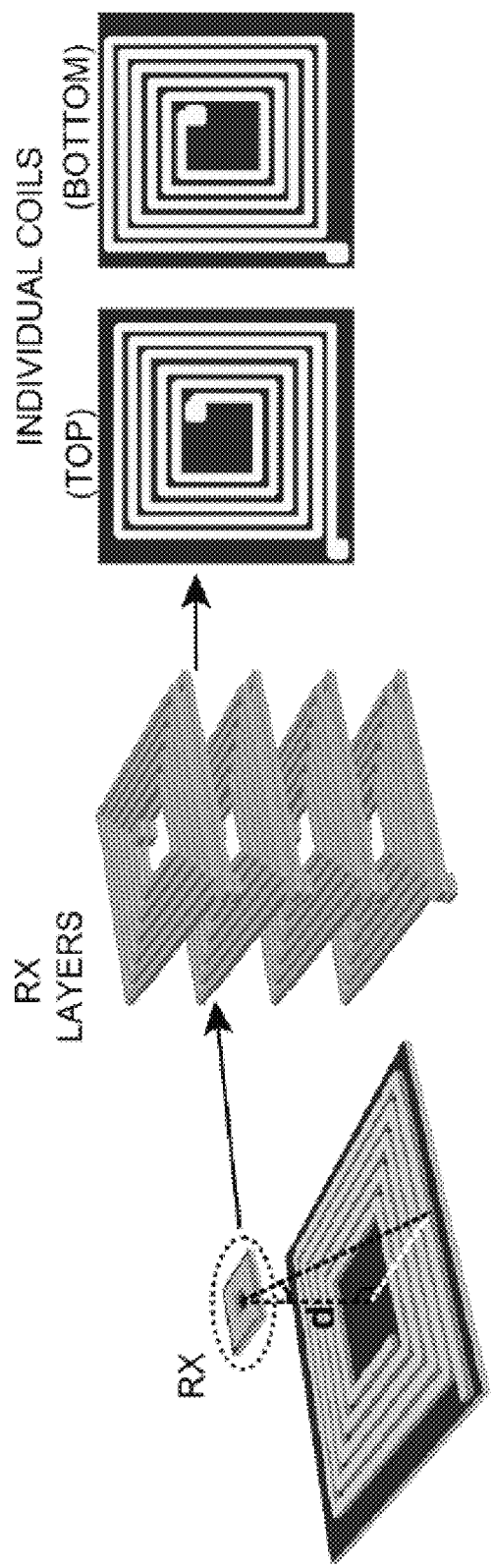
FIG. 17 illustrates a coil stacking arrangement.

FIG. 17 illustrates a method of fabricating high-inductance high-quality-factor planar inductors without increasing the available number of metal layers (e.g. copper layers) or thickness of the available metal layers in the fabrication process. Inductance and quality factor may be simultaneously multiplied by stacking multiple planar spiral inductors such that the last turn of an inductor on a layer is connected to the first turn of the inductor on the next layer while maintaining the same direction of rotation of the turns going from one turn to the next.

Figure 18:
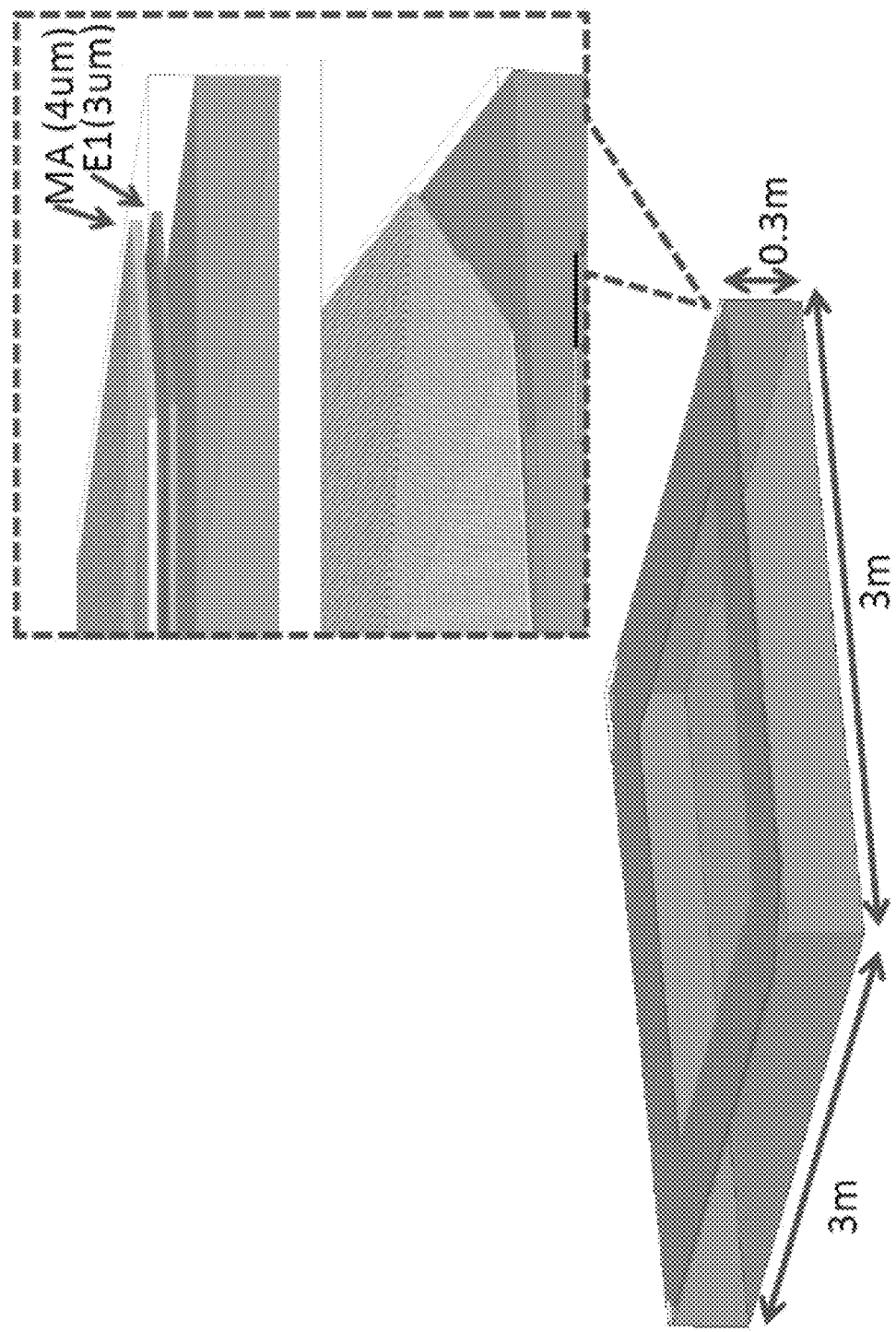
FIG. 18 illustrates an exemplary design of integrated inductors on a CMOS substrate.

FIG. 18 illustrates the same stacked RX coil design technique as in FIG. 17, where the coil may be fabricated on an integrated circuit (IC) substrate instead of a PCB substrate. Energy may be harvested inductively to power the sensors and/or data processing circuits of the chip. To obtain the maximum level of power from the coil, the turns may be traced in series with minimum allowable width and spacing on all of the thick metal layers of the semiconductor technology while the thinner lower metal layer may be used to fabricate peripheral power and data processing circuits directly underneath the RX coil, including rectifiers, storage n-well capacitors, voltage limiter, regulators, array readout circuits including multiplexers and decoders, and clock and data recovery circuits.

An area in the center of the semiconductor chip may be left untraced, which is the size of the minimum area required to fabricate the sensor array or any other on-chip circuits that uses at least one of the thick metal layers in its layout (including MIM capacitors, and spiral inductors other than the RX coil).

Although the invention has been described with reference to certain specific embodiments, various modifications thereof will be apparent to those skilled in the art. The scope of the claims should not be limited by the preferred embodiments, but should be given the broadest interpretation consistent with the description as a whole.

The invention claimed is:

1. An electronic device for continuous and simultaneous powering and data transfer, the electronic device comprising:
    an inductive power receiver comprising:
        a resonator having an inductive receiving coil for receiving an externally induced magnetic field and correspondingly generating a resonating current;
        a rectifier electrically coupled to the resonator to convert and store a portion of the resonating current to a DC voltage; and
        a data transmitter coupled to the inductive power receiver, the data transmitter comprising:
    clipping diodes for limiting a power signal received from the inductive power receiver to a threshold voltage to produce a clipped signal; and
    an antenna electrically coupled to the clipping diodes and configured to emit a pulse train corresponding to the clipped signal.

2. The electronic device of claim 1, wherein the resonating current resonates at the frequency of the externally induced magnetic field.

3. The electronic device of claim 1, wherein the data transmitter further comprises an LC tank, and the clipping diodes comprise a diode pair, the LC tank and diode pair cooperating to generate the clipped signal.

4. The electronic device of claim 1, further comprising a high-pass filter to filter the clipped signal and create the pulse train.

5. The electronic device of claim 1, wherein the pulse train is usable for data transmission.

6. The electronic device of claim 1, wherein the threshold voltage is digitally controlled with one or more digital to analogue converters.

7. The electronic device of claim 1, wherein the power signal comprises an alternating current voltage.

8. The electronic device of claim 1, wherein the data transmitter further comprises a resonating coil coupled to the inductive receiving coil.

* * * * *